US006590076B1

(12) United States Patent
Yuqiu et al.

(10) Patent No.: US 6,590,076 B1
(45) Date of Patent: Jul. 8, 2003

(54) COMPOSITIONS FOR THE TREATMENT AND DIAGNOSIS OF BREAST CANCER AND METHODS FOR THEIR USE

(75) Inventors: Jiang Yuqiu, Kent, WA (US); Davin C. Dillon, Redmond, WA (US); Jennifer L. Mitcham, Redmond, WA (US); Jiangchun Xu, Bellevue, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/285,480

(22) Filed: Apr. 2, 1999

Related U.S. Application Data

(63) Continuation-in-part of application No. 09/222,575, filed on Dec. 28, 1998, now Pat. No. 6,387,697.

(51) Int. Cl.[7] .............................................. C07K 14/00

(52) U.S. Cl. ................. 530/350; 424/184.1; 424/193.1; 424/278.1; 536/23.1; 536/23.4; 514/2

(58) Field of Search ............................ 514/2; 530/350; 536/23.1, 23.4; 424/184.1, 193.1, 278.1

(56) References Cited

U.S. PATENT DOCUMENTS

| | | | | |
|---|---|---|---|---|
| 5,215,926 A | 6/1993 | Etchells, III et al. | ....... | 436/501 |
| 5,240,856 A | 8/1993 | Goffe et al. | ................ | 435/299 |
| 5,891,857 A | 4/1999 | Holt et al. | .................... | 514/44 |
| 5,986,170 A | 11/1999 | Subjeck | ......................... | 800/2 |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/21331 | 5/1998 |
| WO | WO 98/33915 | 8/1998 |
| WO | WO 98/54963 | 12/1998 |
| WO | WO 99/09155 | 2/1999 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |

OTHER PUBLICATIONS

1/ Burgers et al. J. Cell Biol. 11:2129–2138 1990.*

2/ Gura. Science, 278: 1041–1042, 1997.*

3/Jain Sci. Am. 271: 58–65, 1994.*

4/ Curti. Crit. Rev. Onwl/Humatol. 14: 29–39, 1993.*

5/ Hartwell. Science 278: 1064–1068 1997.*

6/ Ezzell J. Nih Res. 7: 46–49, 1995.*

7/ Spitler. Cancer Biotherapy 10: 1–3 1995.*

8/ Boon. Adv. Cancer Res 58: 177–210, 1992.*

9/ Lazar. Mol. Cell. Biol. 8: 1247–1252, 1988.*

10/ Tao et al. J. Immunol. 143(8): 2595–2601, 1989.*

11/ Gillies Human Antibod & Hybridomas 1(1): 47–54, 1990.*

12/ Ravie et al. Accession No. V 90219. GenBank, and MPSRCH search report, p. 1–2, 1998.*

13/ Adams et al.. Acession No. AQ280806, GenBank, and MPSRCH search report p. 3, 1998.*

14/ NCI–CGAP—Accession No. AI 687645. genBank and MPSRCH search, p. 3.*

1/ Alberts et al. Mol. Biol. Cell, 3rd ed., p. 455, 1994.*

2/ Shantz. et al. J. Biochem. Cell Biol. 31: 107–122, 1999.*

3/ McClean et al. Eur. J. Cancer, 29A: 2243–2248, 1993.*

4/ Fu et al. EMBO J. 15: 4392–4401, 1996.*

5/ Freshney, Cult. Animal Cells, A manual of Basic Technique, Alan R. Lisc. Inc. p. 4, 1983.*

6/Dermer. Bio/Technol. 12:320, 1994.*

GenBank Accession No. AC069200, May 24, 2000.

Sulston et al., "Toward a complete human genome sequence," *Genome Research 8*(11):1097–1108, 1998.

GenBank Accession No. AL157387, Feb. 18, 2000.

GenBank Accession No. AC036170, Apr. 9, 2000.

Jäger, D. et al, "Identification of a Tissue–specific Putative Transcription Factor in Breast Tissue by Serological Screening of a Breast Cancer Library," *Cancer Research 61*(5):2055–2061, Mar. 1, 2001.

GenBank Accession No. AF269087, Mar. 28, 2001.

GenBank Accession No. AAK27325, Mar. 28, 2001.

Chang and Shu, "Current status of adoptive immunotherapy of cancer," *Critical Reviews in Oncology/Hematology 22*(3):213–228, Apr. 1996.

Cheever and Chen, "Therapy with cultured T cells: principles revisited," *Immunological Reviews, 157* : 177–194, 1997.

Cheever et al., "Potential uses of interleukin 2 in cancer therapy," *Immunobiol, 172*:365–382, 1986.

Cole et al., "Characterization of the functional specificity of a cloned T–cell receptor heterodimer recognizing the MART–1 melanoma antigent," *Cancer Research, 55*:748–752, Feb. 15, 1995.

Durrant L., "Cancer vaccines," *Anti–Cancer Drugs, 8*:727–733, 1997.

(List continued on next page.)

*Primary Examiner*—Anthony C. Caruta
*Assistant Examiner*— Minh Tam Davis
(74) *Attorney, Agent, or Firm*—Seed Intellectual Property Law Group PLLC

(57) ABSTRACT

Compounds and methods for the treatment and diagnosis of breast cancer are provided. The inventive compounds include polypeptides containing at least a portion of a breast tumor antigen. Vaccines and pharmaceutical compositions for immunotherapy of breast cancer comprising such polypeptides, or polynucleotides encoding such polypeptides, are provided, together with polynucleotides for preparing the inventive polypeptides. The inventive polypeptides may be used to generate antibodies useful for the diagnosis and monitoring of breast cancer.

9 Claims, 1 Drawing Sheet

OTHER PUBLICATIONS

Figure 1:
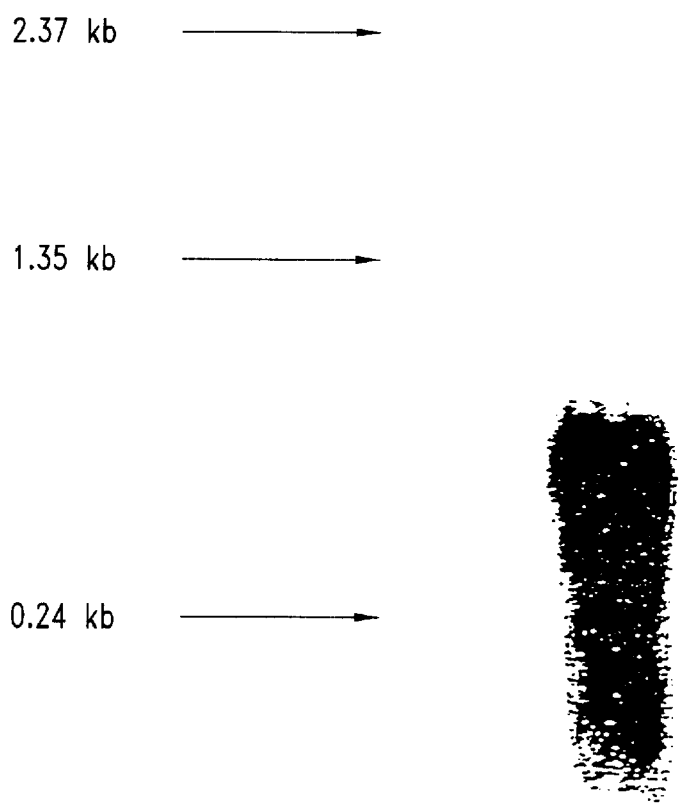

Eshhar Z., "Tumor–specific T–bodies: toward clinical applications," *Cancer Immunol Immunother, 45*:131–136, 1997.
Hwu et al., "In vivo antitumor activity of T cells redirected with chimeric antibody/T–cell receptor genes," *Cancer Research, 55*:3369–3373, Aug. 1, 1995.
Porter–Jordan and Lippman, "Overview of the biologic markers of breast cancer," *Breast Cancer 8*:(1):73–100, Feb. 1994.
Wei et al., "Protection against mammary tumor growth by vaccination with full–length, modified human ErbB–2 DNA," *Int. J. Cancer, 81*:748–754, 1999.
GenBank Accession No. AA864891, Feb. 20, 1998.
GenBank Accession No. AA398925, Apr. 25, 1997.
Geneseq Accession No V84525 (Dec. 10 1998).
Stratagene 1991 product catalog, Prime–It™ Random Labeling Kit, catalog No. 300387, p. 66.

* cited by examiner

SYN18C6 NORTHERN BLOT

COMPOSITIONS FOR THE TREATMENT AND DIAGNOSIS OF BREAST CANCER AND METHODS FOR THEIR USE

CROSS-REFERENCE TO RELATED APPLICATIONS

This application is a continuation-in-part of U.S. application Ser. No. 09/222,575, filed Dec. 28, 1998, now U.S. Pat. No. 6,387,697.

TECHNICAL FIELD

The present invention relates generally to compositions and methods for the treatment of breast cancer. The invention is more particularly related to polypeptides comprising at least a portion of a protein that is preferentially expressed in breast tumor tissue and to polynucleotides encoding such polypeptides. Such polypeptides and polynucleotides may be used in vaccines and pharmaceutical compositions for treatment of breast cancer.

BACKGROUND OF THE INVENTION

Breast cancer is a significant health problem for women in the United States and throughout the world. Although advances have -been made in detection and treatment of the disease, breast cancer remains the second leading cause of cancer-related deaths in women, affecting more than 180, 000 women in the United States each year. For women in North America, the life-time odds of getting. breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

The present invention provides compounds and methods for the treatment and diagnosis of breast cancer. In one aspect, isolated polypeptides are provided comprising at least an immunogenic portion of a breast tumor antigen or a variant thereof, wherein the antigen comprises an amino acid sequence encoded by a polynucleotide having a sequence selected from the group consisting of: (a) nucleotide sequences recited in SEQ ID NO: 1–61, 63–175, 178 and 180; (b) complements of said nucleotide sequences; and (c) sequences that hybridize to a sequence of (a) or (b) under moderately stringent conditions. In specific embodiments, the inventive polypeptides comprise an amino acid sequence selected from the group consisting of SEQ ID NO: 62, 176, 179 and 181.

In related aspects, isolated polynucleotides encoding the above polypeptides are provided. In specific embodiments, such polynucleotides comprise a sequence selected from the group consisting of sequences provided in SEQ ID NO: 1–61, 63–175, 178 and 180. The present invention further provides expression vectors comprising the above polynucleotides, together with host cells transformed or transfected with such expression vectors. In preferred embodiments, the host cells are selected from the group consisting of *E. coli*, yeast and mammalian cells.

In another aspect, the present invention provides fusion proteins comprising a first and a second inventive polypeptide or, alternatively, an inventive polypeptide and a known breast tumor antigen.

The present invention also provides pharmaceutical compositions comprising at least one of the above polypeptides, or a polynucleotide encoding such a polypeptide, and a physiologically acceptable carrier, together with vaccines comprising at least one such polypeptide or polynucleotide in combination with a non-specific immune response enhancer. Pharmaceutical compositions and vaccines comprising one or more of the above fusion proteins are also provided.

In yet another aspect, methods are provided for inhibiting the development of breast cancer in a patient, comprising administering an effective amount of at least one of the above pharmaceutical compositions and/or vaccines.

The polypeptides disclosed herein may be usefully employed in the diagnosis and monitoring of breast cancer. In one aspect of the present invention, methods are provided for detecting breast cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of breast cancer in a; patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides methods for detecting breast cancer comprising: (a) obtaining a biological sample from a patient; (b) contacting the sample with a first and a second oligonucleotide primer in a polymerase chain reaction, at least one of the oligonucleotide primers being specific for a polynucleotide that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a polynucleotide comprising a sequence selected from the group consisting of SEQ ID NO: 1–61, 63–175, 178 and 180.

In a further aspect, the present invention provides a method for detecting breast cancer in a patient comprising: (a) obtaining a biological sample from the patient; (b)

contacting the sample with an oligonucleotide probe specific for a polynucleotide that encodes one of the above polypeptides; and (c) detecting in the sample a DNA sequence that hybridizes to the oligonucleotide probe. Preferably, the oligonucleotide probe comprises at least about 15 contiguous nucleotides of a polynucleotide comprising a sequence selected from the group consisting of SEQ ID NO: 1–61, 63–175, 178 and 180.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

BRIEF DESCRIPTION OF THE DRAWING AND SEQUENCE IDENTIFIERS

FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 11 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence of JBTT18.

SEQ ID NO: 24 is the determined cDNA sequence of JBTT19.

SEQ ID NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6.

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6-2.

SEQ ID NO: 46 is the determined cDNA sequence of SYN21B9.

SEQ ID NO: 47 is the determined cDNA sequence of SYN21 B9-2.

SEQ ID NO: 48 is the determined cDNA sequence of SYN21 C10.

SEQ ID NO: 49 is the determined cDNA sequence of SYN21G10.

SEQ ID NO: 50 is the determined cDNA sequence of SYN21G10-2.

SEQ ID NO: 51 is the determined cDNA sequence of SYN21G11.

SEQ ID NO: 52 is the determined cDNA sequence of SYN21G11-2.

SEQ ID NO: 53 is the determined cDNA sequence of SYN21H8.

SEQ ID NO: 54 is the determined cDNA sequence of SYN22A10.

SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6.

SEQ ID NO: 63 is the determined cDNA sequence of B723P.

SEQ ID NO: 64 is the determined cDNA sequence for B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NOS: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 102 is the determined cDNA sequence of 13140.

SEQ ID NO: 132 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051

SEQ ID NO: 118 is the determined cDNA sequence of 13052

SEQ ID NO: 119 is the determined cDNA sequence of 13055

SEQ ID NO: 120 is the determined cDNA sequence of 13058

SEQ ID NO: 121 is the determined cDNA sequence of 13062

SEQ ID NO: 122 is the determined cDNA sequence of 13064

SEQ ID NO: 123 is the determined cDNA sequence of 13080

SEQ ID NO: 124 is the determined cDNA sequence of 13093

SEQ ID NO: 125 is the determined cDNA sequence of 13094

SEQ ID NO: 126 is the determined cDNA sequence of 13095

SEQ ID NO: 127 is the determined cDNA sequence of 13096

SEQ ID NO: 128 is the determined cDNA sequence of 13099

SEQ ID NO: 129 is the determined cDNA sequence of 13100

SEQ ID NO: 130 is the determined cDNA sequence of 13103

SEQ ID NO: 131 is the determined cDNA sequence of 13106

SEQ ID NO: 132 is the determined cDNA sequence of 13107

SEQ ID NO: 133 is the determined cDNA sequence of 13108

SEQ ID NO: 134 is the determined cDNA sequence of 13121

SEQ ID NO: 135 is the determined cDNA sequence of 13126

SEQ ID NO: 136 is the determined cDNA sequence of 13129

SEQ ID NO: 137 is the determined cDNA sequence of 13130

SEQ ID NO: 138 is the determined cDNA sequence of 13134

SEQ ID NO: 139 is the determined cDNA sequence of 13141

SEQ ID NO: 140 is the determined cDNA sequence of 13142

SEQ ID NO: 141 is the determined cDNA sequence of 14376

SEQ ID NO: 142 is the determined cDNA sequence of 14377

SEQ ID NO: 143 is the determined cDNA sequence of 14383

SEQ ID NO: 144 is the determined cDNA sequence of 14384

SEQ ID NO: 145 is the determined cDNA sequence of 14387

SEQ ID NO: 146 is the determined cDNA sequence of 14392

SEQ ID NO: 147 is the determined cDNA sequence of 14394

SEQ ID NO: 148 is the determined cDNA sequence of 14398

SEQ ID NO: 149 is the determined cDNA sequence of 14401

SEQ ID NO: 150 is the determined cDNA sequence of 14402

SEQ ID NO: 151 is the determined cDNA sequence of 14405

SEQ ID NO: 152 is the determined cDNA sequence of 14409

SEQ ID NO: 153 is the determined cDNA sequence of 14412

SEQ ID NO: 154 is the determined cDNA sequence of 14414

SEQ ID NO: 155 is the determined cDNA sequence of 14415

SEQ ID NO: 156 is the determined cDNA sequence of 14416

SEQ ID NO: 157 is the determined cDNA sequence of 14419

SEQ ID NO: 158 is the determined cDNA sequence of 14426

SEQ ID NO: 159 is the determined cDNA sequence of 14427

SEQ ID NO: 160 is the determined cDNA sequence of 14375

SEQ ID NO: 161 is the determined cDNA sequence of 14378

SEQ ID NO: 162 is the determined cDNA sequence of 14379

SEQ ID NO: 163 is the determined cDNA sequence of 14380

SEQ ID NO: 164 is the determined cDNA sequence of 14381

SEQ ID NO: 165 is the determined cDNA sequence of 14382

SEQ ID NO: 166 is the determined cDNA sequence of 14388

SEQ ID NO: 167 is the determined cDNA sequence of 14399

SEQ ID NO: 168 is the determined cDNA sequence of 14406

SEQ ID NO: 169 is the determined cDNA sequence of 14407

SEQ ID NO: 170 is the determined cDNA sequence of 14408

SEQ ID NO: 171 is the determined cDNA sequence of 14417

SEQ ID NO: 172 is the determined cDNA sequence of 14418

SEQ ID NO: 173 is the determined cDNA sequence of 14423

SEQ ID NO: 174 is the determined cDNA sequence of 14424

SEQ ID NO: 175 is the determined cDNA sequence of B726P-20

SEQ ID NO: 176 is the predicted amino acid sequence of B726P-20

SEQ ID NO: 177 is a PCR primer

SEQ ID NO: 178 is the determined cDNA sequence of B726P-74

SEQ ID NO: 179 is the predicted amino acid sequence of B726P-74

SEQ ID NO: 180 is the determined cDNA sequence of B726P-79

SEQ ID NO: 181 is the predicted amino acid sequence of B726P-79

DETAILED DESCRIPTION OF THE INVENTION

As noted above, the present invention is generally directed to compositions and methods for the treatment and diagnosis of breast cancer. The inventive compositions are generally isolated polypeptides that comprise at least a portion of a breast tumor antigen. Also included within the present invention are molecules (such as an antibody or fragment thereof) that bind to the inventive polypeptides. Such molecules are referred to herein as "binding agents."

In particular, the subject invention discloses polypeptides comprising at least a portion of a human breast tumor antigen, or a variant thereof, wherein the breast tumor antigen includes an amino acid sequence encoded by a polynucleotide including a sequence selected from the group consisting of: nucleotide sequences recited in SEQ ID NO:

1–61, 63–175, 178 and 180, the complements of said nucleotide sequences, and variants thereof. As used herein, the term "polypeptide" encompasses amino acid chains of any length, including full length proteins, wherein the amino acid residues are linked by covalent peptide bonds. Thus, a polypeptide comprising a portion of one of the above breast antigens may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human breast tumor antigen is a portion that is capable of eliciting an immune response in a patient inflicted with breast cancer and as such binds to antibodies present within sera from a breast cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$-labeled Protein A. Alternatively, a polypeptide may be used to generate monoclonal and polyclonal antibodies for use in detection of the polypeptide in blood or other fluids of breast cancer patients. Methods for preparing and identifying immunogenic portions of antigens of known sequence are well known in the art and include those summarized in Paul, *Fundamental Immunology*, 3$^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a polynucleotide in a generally one-to-one manner. An mRNA molecule corresponds to an HnRNA and polynucleotide from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. Such variants include, but are not limited to, naturally occurring allelic variants of the inventive sequences.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The breast tumor antigens provided by the present invention include variants that are encoded by DNA sequences which are substantially homologous to one or more of the DNA sequences specifically recited herein. "Substantial homology," as used herein, refers to DNA sequences that are capable of hybridizing under moderately. stringent conditions. Suitable moderately stringent conditions include prewashing in a solution of 5×SSC; 0.5% SDS, 1.0 mM EDTA (pH 8:0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as. are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol*. 4:406–425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

The breast tumor antigens of the present invention, and polynucleotides encoding such antigens, may be isolated from breast tumor tissue using any of a variety of methods well known in the art. DNA sequences corresponding to a gene (or a portion thereof) encoding one of the inventive breast tumor antigens may be isolated from a breast tumor cDNA library using a subtraction technique as described in detail below. Examples of such DNA sequences are provided in SEQ ID NO: 1–61, 63–175, 178 and 180. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol*., 51:263, 1987; Erlich ed., PCR Technology, Stockton Press, N.Y., 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA*, 2:183,1983).

The breast tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc*. 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure, form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known breast tumor antigen, together with variants of such fusion proteins.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. PIeptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91 (1997)).

Polypeptides of the present invention that comprise an immunogenic portion of a breast tumor antigen may generally be used for immunotherapy of breast cancer, wherein the polypeptide stimulates the patient's own immune response to breast tumor cells. The present invention thus provides methods for using one or more of the immunoreactive polypeptides encoded by a polynucleotide comprising a sequence of SEQ ID NO: 1–61, 63–175, 178 and 180 (or fusion proteins comprising one or more such polypeptides and/or DNA encoding such polypeptides) for immunotherapy of breast cancer in a patient. As used herein, a "patient" refers to any warm-blooded animal., preferably a human. A patient may be afflicted with a disease, or may be free of detectable disease. Accordingly, the above immunoreactive polypeptides (or fusion proteins or polynucleotides encoding such polypeptides) may be used to treat breast cancer or to inhibit the development of breast cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the inventive sequences (or variants thereof), and a physiologically acceptable carrier. The vaccines may comprise one or more such polypeptides and a non-specific immune response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus-Calmette-Guerrin*) that expresses an epitope of a breast tumor cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et. al., *Ann. N.Y. Acad Sci*. 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res*. 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against breast tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune F-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast or B-cells, may be pulsed with immunoreactive polypeptides or polynucleotide sequence(s) may be introduced into antigen presenting cells, using standard techniques well known in the art. For example, antigen presenting cells may be transfected or transduced with a polynucleotide sequence, wherein said sequence contains a promoter region appropriate for inducing expression, and can be expressed as part of a recombinant virus or other expression system. Several viral vectors may be used to transduce an antigen presenting cell, including pox virus, vaccinia virus, and adenovirus. Antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever et al. Ibid).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol*., 22(3), 213, 1996). Cells of the immune system, such as T cells, may be isolated from the peripheral blood of a patient, using a commercially available cell separation system. The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res*, 55(15):3369–73, 1995. Another embodiment may include the transfection of tumor antigen specific alpha and beta T cell receptor chains into alternate T cells, as in Cole, D J, et al, *Cancer Res*, 55(4):748–52, 1995.

In further embodiments, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. ("Therapy With Cultured T Cells: Principles Revisited," *Immunological Reviews*, 157:177, 1997). Additionally vectors expressing the disclosed polynucleotides may be introduced into stem cells taken from the patient and clonally propagated in vitro for autologous transplant back into the same patient.

In one specific embodiment, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Additionally vectors expressing the disclosed polynucleotides may be introduced into stem cells taken from the patient and clonally propagated in vitro for autologous transplant back into the same patient.

Polypeptides of the present invention may also, or alternatively, be used to generate binding agents, such as antibodies or fragments thereof, that are capable of detecting metastatic human breast tumors. Binding agents of the present invention may generally be prepared using methods known to those of ordinary skill in the art, including the representative procedures described herein. Binding agents are capable of differentiating between patients with and without breast cancer, using the representative assays described herein. In other words, antibodies or other binding agents raised against a breast tumor antigen, or a suitable portion thereof, will generate a signal indicating the presence of primary or metastatic breast cancer in at least about 20% of patients afflicted with the disease, and will generate a negative signal indicating the absence of the disease in at least about 90% of individuals without primary or metastatic breast cancer. Suitable portions of such breast tumor antigens are portions that are able to generate a binding agent that indicates the presence of primary or metastatic breast cancer in substantially all (i.e., at least about 80%, and preferably at least about 90%) of the patients for which breast cancer would be indicated using the full length antigen, and that indicate the absence of breast cancer in substantially all of those samples that would be negative when tested with full length antigen. The representative assays described below, such as the two-antibody sandwich assay, may generally be employed for evaluating the ability of a binding agent to detect metastatic human breast tumors.

The ability of a polypeptide prepared as described herein to generate antibodies capable of detecting primary or metastatic human breast tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic breast cancer for the presence of a polypeptide that binds to the generated antibodies. Such test assays may be performed, for example, using a representative procedure described below. Polypeptides that generate antibodies capable of detecting at least 20% of primary or metastatic breast tumors by such procedures are considered to be useful in assays for detecting primary or metastatic human breast tumors. Polypeptide specific antibodies may be used alone or in combination to improve sensitivity.

Polypeptides capable of detecting primary or metastatic human breast tumors may be used as markers for diagnosing breast cancer or for monitoring disease progression in patients. In one embodiment, breast cancer in a patient may be diagnosed by evaluating a biological sample obtained from the patient for the level of one or more of the above polypeptides; relative to a predetermined cut-off value. As used-herein, suitable "biological samples" include blood, sera and urine.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For exarnple, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or TWEEN 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using. standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without breast cancer. In general, a sample generating a signal that is three standard deviations above the predetermined cut-off value is considered positive for breast cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of breast cancer. In this embodiment,. assays as described above for the diagnosis of breast cancer may be performed over time, and the change in the level of reactive polypeptide(s) evaluated. For example, the assays may be performed every 24–72 hours for a period of 6 months to 1 year, and thereafter performed as needed. In general, breast cancer is progressing in those patients in whom the level of polypeptide detected by the binding agent increases over time. In contrast, breast cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate breast tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulflhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody-molecule. In another embodiment, more than one type of agent may be coupled to one antibody. Regardless of the particular embodiment, immunoconjugates with, more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify breast tumor-specific cDNA derived from a biological sample, wherein at least one of the oligonucleotide primers is specific for a polynucleotide encoding a breast tumor protein of the present invention. The presence of the amplified cDNA is then detected using techniques well known in the art, such as gel electrophoresis. Similarly, oligonucleotide probes specific for a polynucleotide encoding a breast tumor protein of the present invention may be used in a hybridiatioin assay to detect the presence of an inventive polypeptide in a biological sample.

As used herein, the term "oligonucleotide primer/probe specific for a polynucleotide" means an oligonucleotide sequence that has at least about 60%, preferably at least about 75% and more preferably at least about 90%, identity to the polynucleotide in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide comprising a sequence selected from SEQ ID NOS: 1–61, 63–175, 178 and 180. Preferably, oligonucleotide probes for use in the inventive diagnostic methods comprise at least about 15 contiguous oligonucleotides of a polynucleotide comprising a sequence provided in SEQ ID NOS: 1–61, 63–175, 178 and 180. Techniques for both PCR based assays and hybridization assays are well known in the art (see, for example, Mullis et al. Ibid; Ehrlich, Ibid). Primers or probes may thus be used to detect breast tumor-specific sequences in biological samples, including blood, urine and/or breast tumor tissue.

The following Examples are offered by way of illustration and not by way of limitation.

EXAMPLES

Example 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total .RNA was extracted from primary tissues using Trizol reagent (Gibco BRL Life Technologies, Gaithersburg, Md.) as described by the manufacturer. The polyA+RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to Clontech's protocol. The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NOS: 1–61, 72 and 73, respectively. Comparison of these cDNA sequences with known sequences in the gene bank using the EMBL and GenBank databases (Release 97) revealed no significant homologies to the sequences provided in SEQ ID NOS: 14, 21, 22, 27, 29, 30, 32, 38, 44, 45, 53, 72 and 73. The sequences of SEQ ID NOS: 1, 3, 16, 17, 34, 48, 57, 60 and 61 were found to represent known human genes, The sequences of SEQ ID NOS: 2, 4, 23, 39 and 50 were found to show some similarity to previously identified non-human genes. The remaining clones (SEQ ID NOS: 5–13, 15, 18–20, 24–26, 28. 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured.

Data was analyzed using Synteni provided GEMTOOLS Software. Of the seventeen cDNA clones examined, those of SEQ ID NOS: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NOS: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NOS: 63–87. Comparison of the sequences of SEQ ID NOS: 74–87 with those in the gene bank as described above, revealed homology to previously identified human genes. No significant homologies were found to the sequences of SEQ ID NOS: 63–73.

Three DNA isoforms for the clone B726P (partial sequence provided in SEQ ID NO: 71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [$\alpha$-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 181.

Example 2

Isolation and Characaterization of Breast Tumor Polypeptides Obtained by PCR-based Subtraction Using Scid-passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, now U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NOS: 88–116, respectively. The isolated cDNA sequences of SEQ ID NOS: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NOS: 141–159, respectively. The isolated cDNA sequences of SEQ ID NOS: 160–174 were found to show homology to previously known genes.

Example 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polypeptide comprising SEQ ID NO: 176.

2. An isolated polypeptide comprising the amino acid sequence encoded by SEQ ID NO: 175.

3. A composition comprising the polypepticle of any one of claims 1 and 2 and a physiologically acceptable carrier.

4. A composition comprising the polypeptide of any one of claims 1 and 2 and a non-specific immune response enhancer.

5. The composition of claim 4 wherein the non-specific immune response enhancer is an adjuvant.

6. A fuision protein comprising at least one polypeptide according to any one of claims 1 and 2.

7. A composition comprising a fusion protein according to claim 6 and a physiologically acceptable carrier.

8. A composition comprising a fusion protein according to claim 6 and a non-specific immune response enhancer.

9. The composition of claim 6 wherein the non-specific immune response enhancer is an adjuvant.

* * * * *

UNITED STATES PATENT AND TRADEMARK OFFICE

CERTIFICATE OF CORRECTION

PATENT NO. : 6,590,076 B1
DATED : July 8, 2003
INVENTOR(S) : Jiang Yuqiu et al.

It is certified that error appears in the above-identified patent and that said Letters Patent is hereby corrected as shown below:

Column 145,
Line 41, "the polypepticle" should read as -- the polypeptide --.

Column 146,
Line 37, "A fuision protein" should read as -- A fusion protein --.
Line 44, "of claim 6" should read as -- of claim 8 --.

Signed and Sealed this

Eighth Day of June, 2004

JON W. DUDAS
*Acting Director of the United States Patent and Trademark Office*

UNITED STATES PATENT AND TRADEMARK OFFICE

CERTIFICATE OF CORRECTION

PATENT NO. : 6,590,076 B1
APPLICATION NO. : 09/285480
DATED : July 8, 2003
INVENTOR(S) : Jiang Yuqiu et al.

It is certified that error appears in the above-identified patent and that said Letters Patent is hereby corrected as shown below:

Title Page Item 63
Related U.S. Application Data should be deleted.

Signed and Sealed this
First Day of March, 2011

David J. Kappos
*Director of the United States Patent and Trademark Office*

SEQUENCE LISTING

```
<160> NUMBER OF SEQ ID NOS: 181

<210> SEQ ID NO 1
<211> LENGTH: 281
<212> TYPE: DNA
<213> ORGANISM: Homo sapien

<400> SEQUENCE: 1

caatgacagt caatctctat cgacagcctg cttcatattt agctattgtt cgtattgcct     60

tctgtcctag gaacagtcat atctcaagtt caaatgccac aacctgagaa gcggtgggct    120

aagataggtc ctactgcaaa ccacccctcc atatttccgt acgcaattac aattcagttt    180

ctgtgacatc tctttacacc actggaggaa aaatgagata ttctctgatt tattctacta    240

taacactcta catagagcta tggtgagtgc taaccacatc g                         281


<210> SEQ ID NO 2
<211> LENGTH: 300
<212> TYPE: DNA
<213> ORGANISM: Homo sapien

<400> SEQUENCE: 2

gaggtcctgg gctaacctaa tggtttatta ttggtggaga gaaagatctg gaaatacttg     60

aggttattac atactagatt agcttctaat gtgaaccatt tttcttttaa cagtgataaa    120

ttattatttc cgaagttaac tgttcccttg gtcgtgatac acactcgatt aacaaacata    180

ctgttgtatt ttttccagtt ttgtttggct atgccaccac agtcatcccc agggtctata    240

catactatgt ctcaactgta ttatttgcca tttttggcat tagaatgctt cgggaaggct    300


<210> SEQ ID NO 3
<211> LENGTH: 302
<212> TYPE: DNA
<213> ORGANISM: Homo sapien

<400> SEQUENCE: 3

ggccgaggta attggttaag tctaaagaga ttattattcc ttgatgtttg ctttgtattg     60

gctacaaatg tgcagaggta atacatatgt gatgtcgatg tctctgtctt tttttttgtc    120

tttaaaaaat aattggcagc aactgtattt gaataaaatg atttcttagt atgattgtac    180

agtaatgaat gaaagtggaa catgtttctt tttgaaaggg agagaattga ccatttattg    240

ttgtgatgtt taagttataa cttatcgagc acttttagta gtgataactg tttttaaact    300

tg                                                                   302


<210> SEQ ID NO 4
<211> LENGTH: 293
```

```
<212> TYPE: DNA
<213> ORGANISM: Homo sapien

<400> SEQUENCE: 4

tgtaccaatc ctttggcaca agaatatgta agaactatag ttgtttttat tggtttttgt     60

tcttgagatt gttttcattc tgtttttgac tgtatctctt taggaggctg aggatggcat    120

tattgcttat gatgactgtg gggtgaaact gactattgct tttcaagcca aggatgtgga    180

aggatctact tctcctcaaa tacgagataa ggcaagataa ttctgctcat tcgagagagg    240

gttaagagtt gtcatcttaa tcataaatcc tgcaggatgg gttcttcaaa ttt          293


<210> SEQ ID NO 5
<211> LENGTH: 275
<212> TYPE: DNA
<213> ORGANISM: Homo sapien

<400> SEQUENCE: 5

cgaggtttgg aatcagactt ctgtgtccag taaaaaactc ctgcactgaa gtcattgtga     60

cttgagtagt tacagactga ttccagtgaa cttgatctaa tttcttttga tctaatgaat    120

gtgtctgctt accttgtctc cttttaattg ataagctcca agtagttgct aatttttga     180

caactttaaa tgagtttcat tcacttcttt tacttaatgt tttaagtata gtaccaataa    240

tttcattaac ctgttctcaa gtggtttagc tacca                               275


<210> SEQ ID NO 6
<211> LENGTH: 301
<212> TYPE: DNA
<213> ORGANISM: Homo sapien

<400> SEQUENCE: 6

gaggtctggt ttcctgggta tgcctggact gttgcccagt gtaagatctg tgcaagccat     60

attggatgga agtttacggc caccaaaaaa gacatgtcac ctcaaaaatt ttggggctta    120

acgcgatctg ctctgttgcc cacgatccca gacactgaag atgaaataag tccagacaaa    180

gtaatacttt gcttgtaaac agatgtgata gagataaagt tatctaacaa attggttata    240

ttctaagatc tgctttggaa attattgcct ctgatacata cctaagtaaa cataacatta    300

a                                                                    301


<210> SEQ ID NO 7
<211> LENGTH: 301
<212> TYPE: DNA
<213> ORGANISM: Homo sapien

<400> SEQUENCE: 7

gtccagtttg tacacagtga ttccttatgc acgccgaaag ggtttccgta aaaatgacat     60

tatatacaaa tctgtacacc catccaccag agcgattctc cagctcccag agggagttat    120

caacttaaag caggatacct gaggtttcat gtctttagtt gccttatcat aatcccaaat    180

atacatttca gggtttgttt ttgtttttaa agacactttc ctggaatatg tgcactatgg    240

ttaaaattaa aaacaaaagt aataaaataa aatgatcgct ggaaggactg acctccccac    300

c                                                                    301


<210> SEQ ID NO 8
<211> LENGTH: 301
<212> TYPE: DNA
<213> ORGANISM: Homo sapien
```

<400> SEQUENCE: 8
ctgtcctcat ctctgcaaag ttcagcttcc ttccccaggt ctctgtgcac tctgtcttgg 60
atgctctggg gagctcatgg gtggaggagt ctccaccaga gggaggctca ggggactggt 120
tgggccaggg atgaatattt gagggataaa aattgtgtaa gagccaaaga attggtagta 180
gggggagaac agagaggagc tgggctatgg gaaatgattt gaataatgga gctgggaata 240
tggctggata tctggtacta aaaaagggtc tttaagaacc tacttcctaa tctcttcccc 300
a 301

<210> SEQ ID NO 9
<211> LENGTH: 301
<212> TYPE: DNA
<213> ORGANISM: Homo sapien

<400> SEQUENCE: 9
gaggtctgcc taagtagagg acaaagactt cctcctttca aaggagaact gagcccagga 60
ttggtaagtt taaggcactt aaccttgacc agctctgtag gtctggagca ttctggtccc 120
tggccgcttt caccaccagg cccttctcac ttatccacct cacatactgc cccagcattc 180
ctttggcatt gcgagctgtg acttgacaca ttttaatgac aagattgaag tagctacctt 240
gcaggataga ttttctgggg tataggggac aaaccaacag tgccatcagg tgtcttaaca 300
c 301

<210> SEQ ID NO 10
<211> LENGTH: 301
<212> TYPE: DNA
<213> ORGANISM: Homo sapien

<400> SEQUENCE: 10
ggcaggtcca acagttcttc cagttctggt cgagctttga atcgtccctt gaagtcttct 60
tcagtgtgct ccttcactga cagtctgact ccttcaggaa gactgctttg gattatttcc 120
aagaaaattt ctgcaaacgt agcactcaaa ccgctgatct gaaccactcg ctcatgggtg 180
gtaagcactg agtccaggag cattttgctg ccttggtcct gcaactgcaa cacttctatg 240
gttttggttg gcattgcata actttcctcg actttaatgg agagagattg cagaggttgt 300
g 301

<210> SEQ ID NO 11
<211> LENGTH: 301
<212> TYPE: DNA
<213> ORGANISM: Homo sapien

<400> SEQUENCE: 11
aggtctgtga ctttcaccca ggacccagga cgcagccctc cgtgggcact gccggcgcct 60
tgtctgcaca ctggaggtcc tccattacag aggcccagcg cacatcgctg gccccacaaa 120
cgttcagggg tacagccatg gcagctcctt cctctgccgt gagaaaagtg cttggagtac 180
ggtttgccac acacgtgact ggacagtgtc caattcaaat ctttcagggc agagtccgag 240
cagcgcttgg tgacagcctg tcctctcctg ctctccaaag gccctgctcc ctgtcctctc 300
t 301

<210> SEQ ID NO 12
<211> LENGTH: 301
<212> TYPE: DNA
<213> ORGANISM: Homo sapien

<400> SEQUENCE: 12
gaggtctggg attacaggca cgtgccacca cacctagcta atttttgagc atggggctca 60
aaggaactgc tctctggggc atgtcagatt tcggatttgg ggctgcacac tgatactctc 120
taagtggtgg aggaacttca tcccactgaa attcctttgg catttggggt tttgtttttc 180 ttttttttcct tcttcatcct cctccttttt taaaagtcaa cgagagcctt cgctgactcc 240
accgaagaag tgcaccactg ggagccaccc cagtgccagg cgcccgtcca gggacacaca 300
c 301

<210> SEQ ID NO 13
<211> LENGTH: 256
<212> TYPE: DNA
<213> ORGANISM: Homo sapien

<400> SEQUENCE: 13
ttttttggca taaaaaacac aatgatttaa tttctaaagc acttatatta ttatggcatg 60
gtttgggaaa caggttatta tattccacat aggtaattat gcagtgcttc tcatggaaaa 120
aatgcttagg tattggcctt ttctctggaa accatatttt tcctttttta ataatcaact 180
aaaatgtata tgttaaaaag cctcatcttt tgattttcaa tatacaaaat gctttcttta 240
aaagaacaag attcaa 256

<210> SEQ ID NO 14
<211> LENGTH: 301
<212> TYPE: DNA
<213> ORGANISM: Homo sapien

<400> SEQUENCE: 14
ggtccttgat agaggaagag gaatatccaa ggcaaagcca ccaccacgtc caacctcctc 60
atcctctacc tttcctgtcc ccagaggtat gagatagacc ccctggcctg gttcctgcac 120
tgtgctaggc ccacagtgga cacttccacc ttaatggaga ataggcccca tggagtggag 180
gtccctcctc catggcctgc aacccaatga ctatgggggt gacacaagtg acctctgccc 240
tgtgatggct caacaccatc acacgcaact gtccagacaa gccccctcaa cgggctgctg 300
t 301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct 60
ctctttctgc ttttctgatc atcctaaagg ctgaatacat cctcctcctg tgtggaggac 120
acgaagcaat actaaaatca atacactcga tcaggtcttc atcagatacc acgtcactgt 180
gggtagagtg ctaattttca acaaatgtgg tgttcttagg gccccacaag gtagtccttt 240
ctcaaggtcg ctgggccac 259

<210> SEQ ID NO 16
<211> LENGTH: 301
<212> TYPE: DNA
<213> ORGANISM: Homo sapien

<400> SEQUENCE: 16

-continued

```
cgaggttgtt cacattttca aataaataat actccccgta agtaataact gcaaccaatc     60

agtgttattc agtgctatgc ctccttgtaa tgggtagtta ttaattattt tcagagcttt    120

ctggaaatac tgtcctaact ggctatgttt aggatctttg ttatctctga agacaaagaa    180

agaactagga ctcttaattt tggggtgctt cttgactctt agttgggaaa ctgaaaatat    240

ttccaacctt ttacccacgt caatggcata ttctgggaat caccaccacc accaccacta    300

c                                                                    301


<210> SEQ ID NO 17
<211> LENGTH: 301
<212> TYPE: DNA
<213> ORGANISM: Homo sapien

<400> SEQUENCE: 17

gcccgggcag gtctggggcc tagggtggct ctttgcaaag ctgaggggca agctaaggaa     60

gccaggcagg tcaggggccc tttcggcctt ctcaagcctc cacctgagtt ctcgtcaatg    120

ccagtctccc tggtatgatt ggggacatta tcagagaaac atctaatagc gcacatctgg    180

gcacccacac tctgcttcag ttgcatccat cctcccaccc caaattcaac tcctgaccca    240

atacaaaaga ctttttttaac caggatttct tcttgcagga aagctgactt ggaaacacgg    300

g                                                                    301


<210> SEQ ID NO 18
<211> LENGTH: 301
<212> TYPE: DNA
<213> ORGANISM: Homo sapien

<400> SEQUENCE: 18

attacaggca cgtgccacca cacctagcta atttttgagc atggggctca aaggaactgc     60

tctctggggc atgtcagatt tcggatttgg ggctgcacac tgatactctc taagtggtgg    120

aggaacttca tcccactgaa attcctttgg catttggggt tttgtttttc tttttttcct    180

tcttcatcct cctccttttt taaaagtcaa cgagagcctt cgctgactcc accgaagaag    240

tgcaccactg gggaccaccc agtgccaggc gcccgtccag ggacacacac agtcttcact    300

g                                                                    301


<210> SEQ ID NO 19
<211> LENGTH: 301
<212> TYPE: DNA
<213> ORGANISM: Homo sapien

<400> SEQUENCE: 19

agaatctctg cactgtcatc aggtacaaca aaagatcaaa cccctgtccc gatgttaact     60

ttttaactta aaagaatgcc agaaaaccca gatcaacact ttccagctac gagccgtcca    120

caaaggccac ccaaaggcca gtcagactcg tgcagatctt attttttaat agtagtaacc    180

acaatacaca gctctttaaa gctgttcata ttcttccccc attaaacacc tgccccgggc    240

ggccaagggc gaattctgca gatatccatc acactggcgg ccgctcgagc atgcatctag    300

a                                                                    301


<210> SEQ ID NO 20
<211> LENGTH: 290
<212> TYPE: DNA
<213> ORGANISM: Homo sapien

<400> SEQUENCE: 20
```

aggttttttt tttttttttt tttttttttt tttttccctt tcaattcatt taatttcaac 60
aatctgtcaa aaaacagcca ataaacaaat actgaattac attctgctgg gtttttttaaa 120 ggctctaaac tataaaaaca tcttgtgtct cccaccctga ccaccctgct acttttccat 180
ataccacagg ccacccataa acacaaagcc agggggtgaa gctgacatgg tctatttgga 240
gccagtaaac aggagggcga taagtcctga taagcactta tggacaatat 290

<210> SEQ ID NO 21
<211> LENGTH: 301
<212> TYPE: DNA
<213> ORGANISM: Homo sapien

<400> SEQUENCE: 21
agaaaggtaa ctgccagcca ggcttgcatt gtttagccag aaattgctgc ttggttctag 60
actctttaaa aaaaaaaaat acccagggtt tgtcatcatt ttcagaggca gagtgccaaa 120
tatcacccaa agctcttgtg tcttttttttt accccttat tttattttta tttattaatt 180
ttttgtgcaa acatcaaatg tcactggtgt tcacagaagg cttttttgac tagccttaaa 240
ttcctgagtc aaaagattaa tcagattttc aggcagtgtt taatcaggtg ctttgtcctg 300
t 301

<210> SEQ ID NO 22
<211> LENGTH: 301
<212> TYPE: DNA
<213> ORGANISM: Homo sapien

<400> SEQUENCE: 22
gacgccatgc accctccggt aaccagcagc cgcctgtcca tcccccaaga ccggaaaggc 60
agcagcagcc cccgggagcc cagggctgtc ctcggtgcat ctggctgcag agggaaattg 120
atgaccttac acagcaacta gcggccatgc agtccttcac tgacaagttc caggaccttt 180
gaagttggag ccagcgtccg gagctgcagc caagcgagtt tcctccttat cctccttagc 240
cagggctttt tctcttccgc tgcatttgcc cccttcccaa cgcaattcaa agcagttgtg 300
a 301

<210> SEQ ID NO 23
<211> LENGTH: 381
<212> TYPE: DNA
<213> ORGANISM: Homo sapien

<400> SEQUENCE: 23
cgaggtccag acagtggacc aagagatacg ctacataaat tggggtttca caattcttac 60
attatttgtc tgtcacagaa gagagctgct tatgattttg aaggggtcag ggagggtggg 120
agttggtaaa gagtagggta tttctataac agatattatt cagtcttatt tcctaagatt 180
ttgttgtaac ttaaggtatc ttgctacagt agacagaatt ggtaatagca acttttaaaa 240
ttgtcattag ttctgcaata ttagctgaaa tgtagtacag aaaagaatgt acatttagac 300
atttgggttc agttgcttgt agtctgtaaa tttaaaacag cttaatttgg tacaggttac 360
acatatggac ctcccgggcg g 381

<210> SEQ ID NO 24
<211> LENGTH: 214
<212> TYPE: DNA
<213> ORGANISM: Homo sapien

<400> SEQUENCE: 24
aatgatgtaa aaattaatca acagggctgc cacttgcgaa tcccctccaa ggatgctgtg 60
caaagggtct cattggtcct gatgaataat cttgtgactg tacatattcc tgggtgcatg 120
tccacaaata ctgaggtata gcctgcatgc cactaaaaat aacaaaggtt tcaggggtgg 180
aaacattgtc caccacactg tcatgaccat cttt 214

<210> SEQ ID NO 25
<211> LENGTH: 302
<212> TYPE: DNA
<213> ORGANISM: Homo sapien

<400> SEQUENCE: 25
gggggcactg agaactccct ctggaattct tggggggtgt tggggagaga ctgtgggcct 60
ggagataaaa cttgtctcct ctaccaccac cctgtacct agcctgcacc tgtcctcatc 120
tctgcaaagt tcagcttcct tccccaggtc tctgtgcact ctgtcttgga tgctctgggg 180
agctcatggg tggaggagtc tccaccagag ggaggctcag gggactggtt gggccaggga 240
tgaatatttg agggataaaa attgtgtaag aagccaaaga aattggtagt agggggggaga 300 ac 302

<210> SEQ ID NO 26
<211> LENGTH: 301
<212> TYPE: DNA
<213> ORGANISM: Homo sapien

<400> SEQUENCE: 26
ttggagaacg cgctgacata ctgctcggcc acagtcagtg aagctgctgc atctccatta 60
tgttgtgtca gagctgcagc caggattcga atagcttcag ctttagcctt ggccttcgcc 120
agaactgcac tggcctctcc tgctgcctga tttatctgtg cagccttttc tgcttcggag 180
gccaggatct gggcctgttt cttcccttct gccacattga tggccgactc tcgggtcccc 240
tcagactcta gaactgtggc ccgtttccgc cgctctgcct ccacctgcat ctgcatagac 300
t 301

<210> SEQ ID NO 27
<211> LENGTH: 301
<212> TYPE: DNA
<213> ORGANISM: Homo sapien

<400> SEQUENCE: 27
aaatcagtca tcacatctgt gaaaagagtg ctagttataa caaatgagat cacaaatttg 60
accattttat tagacaccct ctattagtgt taacagacaa agatgaaggt taagttgaaa 120
tcaaattgaa atcatcttcc ctctgtacag attgcaatat ctgataatac cctcaacttt 180
cttggtgcaa attaattgcc tggtactcac agtccagtgt taacaggcaa taatggtgtg 240
attccagagg agaggactag gtggcaggaa aataaatgag attagcagta tttgacttgg 300
a 301

<210> SEQ ID NO 28
<211> LENGTH: 286
<212> TYPE: DNA
<213> ORGANISM: Homo sapien

<400> SEQUENCE: 28
tttttttttg cacaggatgc acttattcta ttcattctcc cccacccttc ccatatttac 60

```
atccttagag gaagagaggg gtaaggtgat aaagtaactg aaggaccgca agacgggtat    120

gtcccttgtt caccaaatgg tcaaagggtc aaagatcgga ggaggtcagg gggtaacgca    180

ggaacaggtg agggcgtttc gccctctctc cctctcccct tttcaacctc ttaatcactg    240

gctaactcgc gacctcatgg gttaattcgt aagcttacac gcgttg                   286


<210> SEQ ID NO 29
<211> LENGTH: 301
<212> TYPE: DNA
<213> ORGANISM: Homo sapien

<400> SEQUENCE: 29

gtcatgttct tgctcttcct tctttacaca tttgagttgt gccttctgtt cttaaagaga     60

ttttcctttg ttcaaaggat ttattcctac catttcacaa atccgaaaat aattgaggaa    120

acaggttaca tcattccaat tttgccttgg gtttgaagag tctctcatgg tggcacagtc    180

ctccagggta gctatgttgt tgggctcccc tacatcccag aagctcagag actttgtcaa    240

aggtgtgccg tccacccatt gccactgacc ctcgacaacc tggtctgaca gtccaataaa    300

a                                                                    301


<210> SEQ ID NO 30
<211> LENGTH: 332
<212> TYPE: DNA
<213> ORGANISM: Homo sapien

<400> SEQUENCE: 30

gagcagaatt gatgcctatg gctccaagtc aaatactgct aatctcattt attttcctgc     60

cacctagtcc tctcctctgg aatcacacca ttattgcctg ttaacactgg actgtgagta    120

ccaggcaatt aatttgcacc aagaaagttg agggtattat cagatattgc aatctgtaca    180

gagggaagat gatttcaatt tgatttcaac ttaaccttca tctttgtctg ttaacactaa    240

tagagggtgt ctaataaaat ggtcaaattt gtgatctcat ttgttataac tagcactctt    300

ttcacagatg tgatgactga tttccagcag ac                                  332


<210> SEQ ID NO 31
<211> LENGTH: 141
<212> TYPE: DNA
<213> ORGANISM: Homo sapien

<400> SEQUENCE: 31

aaaggctatc aagtactttg aaggacagga aggaatgaac acacccaggt ggacgtttgg     60

tttcatttgc aggggttcag ggagggttgc aggggttcag ggagggctct tgtcccacaa    120

ccgggggaag ggagagggca c                                              141


<210> SEQ ID NO 32
<211> LENGTH: 201
<212> TYPE: DNA
<213> ORGANISM: Homo sapien

<400> SEQUENCE: 32

gagctgatct cacagcacat acagaatgat gctactatgt agaccctcac tcccttggga     60

aatctgtcat ctaccttaaa gagagaaaaa agatggaaca taggcccacc tagtttcatc    120

catccaccta cataaccaac atagatgtga ggtccactgc actgatagcc agactgcctg    180

gggtaaacct tttcagggag g                                              201
```

<210> SEQ ID NO 33
<211> LENGTH: 181
<212> TYPE: DNA
<213> ORGANISM: Homo sapien

<400> SEQUENCE: 33
tttcaaaaca ctcatatgtt gcaaaaaaca catagaaaaa taaagtttgg tgggggtgct 60
gactaaactt caagtcacag acttttatgt gacagattgg agcagggttt gttatgcatg 120
tagagaaccc aaactaattt attaaacagg atagaaacag gctgtctggg tgaaatggtt 180
c 181

<210> SEQ ID NO 34
<211> LENGTH: 151
<212> TYPE: DNA
<213> ORGANISM: Homo sapien

<400> SEQUENCE: 34
atgtcctgca cagtatagct tggacctctg ggcctgaacc agggtgagca tcaaggcccc 60
catttctcct caccacgggg tcgcttgtca gctccaagaa ccagtctggc cccactgaga 120
acttttcagt cgagggcctg atgaatcttg g 151

<210> SEQ ID NO 35
<211> LENGTH: 291
<212> TYPE: DNA
<213> ORGANISM: Homo sapien

<400> SEQUENCE: 35
tctttagggc aaaatcatgt ttctgtgtac ctagcaatgt gttcccattt tattaagaaa 60
agctttaaca cgtgtaatct gcagtcctta acagtggcgt aattgtacgt acctgttgtg 120
tttcagtttg tttttcacct ataatgaatt gtaaaaacaa acatacttgt ggggtctgat 180
agcaaacata gaaatgatgt atattgtttt ttgttatcta tttattttca tcaatacagt 240
attttgatgt attgcaaaaa tagataataa tttatataac aggttttctg t 291

<210> SEQ ID NO 36
<211> LENGTH: 201
<212> TYPE: DNA
<213> ORGANISM: Homo sapien

<400> SEQUENCE: 36
ctgatacaat tataataacg gttccctgaa ccttttagag tgcaattaag aacaaaaact 60
aaattttgtt tacatgaata tggaataaat acaataatca aaatatgact ctccctaaaa 120
gtgaaacaca caagccaatc cggaactgct gtgcgaaaga taaaatcgag aaaggcaagg 180
tttcggtagg aggacgcgat g 201

<210> SEQ ID NO 37
<211> LENGTH: 121
<212> TYPE: DNA
<213> ORGANISM: Homo sapien

<400> SEQUENCE: 37
catcacactg gcggccgctc gagcatgcat ctagagggcc caattcgccc tataatgagt 60
cgtattacaa ttcactggcc gtcgttttac aacgtcgtga ctgggaaaac cctggcgtta 120
c 121

<210> SEQ ID NO 38
<211> LENGTH: 200
<212> TYPE: DNA
<213> ORGANISM: Homo sapien

<400> SEQUENCE: 38
aaacatgtat tactctatat ccccaagtcc tagagcatga cctgcatgtt ggagatgttg 60
tacagcaatg tatttatcca gacatacata tatgatattt agagacacag tgattctttt 120
gataacacca cacatagaac attataatta cacacaaatt tatggtaaaa gaattaatat 180
gctgtctggt gctgctgtta 200

<210> SEQ ID NO 39
<211> LENGTH: 760
<212> TYPE: DNA
<213> ORGANISM: Homo sapien

<400> SEQUENCE: 39
gcgtggtcgt cggccgaggt cctgggctag acctaatggt ttattattgg tggagagaaa 60
gatctggaaa tacttgaggt tattacatac tagattagct tctaatgtga accatttttc 120
ttttaacagt gatcaaatta ttatttcgaa gttaatcgtt cccttggtgg ctgcatacac 180
atcgcattaa caaacatact gttgtatttt ttcccagttt tgtttggcta tgccaccaca 240
gtcatcccca gggtctatac atactatgtt tcaactgtat tatttgccat ttttggcatt 300
agaatgcttc gggaaggctt aaagatgagc cctgatgagg gtcaagagga actggaagaa 360
gttcaagctg aattaaagaa gaaagatgaa gaagtaagcc atggcactgt tgatctggac 420
caaaaaggca ctcaactagg aataaacact ctacagaggt ttctcagtgg ccccatctgt 480
gtgatatgcg gggctacaca aaaatagctt cttttgcttt gttctgttct tatacctgtc 540
tgtgatctga cttggggttg gtgtgaatgt agtagagaaa ggaagctgac agatgaatac 600
tgaacacagg taatcagttt ccttaattag gttgattata agctcctgaa aagcaggaac 660
tgtattttat aattttacct gtttctcccg tggtgtctag gatagtaagt gagcagagca 720
gtaaatactg tttggtttgt tcagacctgc ccgggcggcc 760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgtttttct 60
tttattaaca ggaattttga ttcttcaagg aagtggctca atttcaattt caggtgacca 120
ggtttatcgt gacttttcct tcttgtttac ttttcgctag gaaggggagt tgtaggggca 180
gattcaggta ttggaatagg aaaattacgt ctaaaccatg gaaatcttgg aaatggaatt 240
ggtggaagtg ggcgaaatgg atatgggtaa gggaacacaa aaaaccctga agctaattca 300
tcgctgtcac tgatacttct tttttctcgt tcctggtctt gagagactgg gaaaccaaca 360
gccactgcca agatggctgt gatcaggagg agaactttct tcatctcaaa cgtttcagtc 420
agttctttct ctcacctcgg ccgcgaccac gc 452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc 60
aagatacata gcaatgatag caggtttctt tttaaagctt agtattaata ttaaatattt 120
ttccccattt aaattttaca ttacttgcca agaaaaaaaa aaaattaaaa ctcaagttac 180
ttgaagcctg gacacacttc catgattagc cgggctaggt aaaagttggt ggctttattc 240
ttcctgctct ataagcagat ccaggcccta gaaagatggg accagggtat ataattgttt 300
ttgaaaagtg tgctacaaaa atggatggcc tgttataagc caggatacaa agttaaggat 360
gggggtaagg gagggacatt ttcttccaga agaaaagaca gaatttctga agagtcccag 420
tccataattt tcccaaaatg gttggaggag agggtaaaat ctcaacatga gtttcaaagt 480
actgtctctg tgaggggccg gtagatgcct tgctgaggag ggatggctaa tttggaccat 540
gccccatccc cagctaggag aatggaaatg gaaactttaa ttgcccagtg ggtgtgaaag 600
tgggctgaag cttggttggt actgaattct ctaagaggtt tcttctagaa acagacaact 660
cagacctgcc cgggcg 676

<210> SEQ ID NO 42
<211> LENGTH: 468
<212> TYPE: DNA
<213> ORGANISM: Homo sapien

<400> SEQUENCE: 42
agcgtggtcg cggccgaggt ttggccggga gcctgatcac ctgccctgct gagtcccagg 60
ctgagcctca gtctccctcc cttggggcct atgcagaggt ccacaacaca cagatttgag 120
ctcagccctg gtgggcagag aggtagggat ggggctgtgg ggatagtgag gcatcgcaat 180
gtaagactcg ggattagtac acacttgttg attaatggaa atgtttacag atccccaagc 240
ctggcaaggg aatttcttca actccctgcc ccccagccct ccttatcaaa ggacaccatt 300
ttggcaagct ctatgaccaa ggagccaaac atcctacaag acacagtgac catactaatt 360 aaaacccccct gcaaagccca gcttgaaacc ttcacttagg aacgtaatcg tgtcccctat 420
cctacttccc cttcctaatt ccacagacct gcccgggcgg ccgctcga 468

<210> SEQ ID NO 43
<211> LENGTH: 408
<212> TYPE: DNA
<213> ORGANISM: Homo sapien

<400> SEQUENCE: 43
atcatatcaa aacactatct tcccatctgt ttctcaatgc ctgctacttc ttgtagatat 60
ttcatttcag gagagcagca gttaaacccg tggattttgt agttaggaac ctgggttcaa 120
acctctttcc actaattggc tatgtctctg gacagttttt tttttttttt tttttttaa 180 accctttctg aactttcact ttctatggct acctcaaaga attgttgtga ggcttgagat 240
aatgcatttg taaagggtct gccagatagg aagatgctag ttatggattt acaaggttgt 300
taaggctgta agagtctaaa acctacagtg aatcacaatg catttacccc cactgacttg 360
gacataagtg aaaactagcc cgaagtctct ttttcaaatt acttacag 408

<210> SEQ ID NO 44
<211> LENGTH: 160
<212> TYPE: DNA
<213> ORGANISM: Homo sapien

<400> SEQUENCE: 44

```
tggtcgcggc cgaggtcttg tgtgccctgt ggtccagggg accaagaaca acaagatcca     60

ctctctgtgc tacaatgatt gcaccttctc acgcaacact ccaaccagga ctttcaacta    120

caacttctcc gctttggcaa acaccgtcac tcttgctgga                          160


<210> SEQ ID NO 45
<211> LENGTH: 231
<212> TYPE: DNA
<213> ORGANISM: Homo sapien

<400> SEQUENCE: 45

cgagcggccg cccgggcagg tctggggagg tgattccatc cagagtcata tctgttgtca     60

ccccaataag tcgatcagca aggctgacag gctgtgagga aaccccggcc ttgtagcctg    120

tcacctctgg ggggatgatg actgcctggc agacgtaggc tgtgatagat ttgggagaaa    180

acctgactca ccctcaggaa tccggaggtc ggtgacattg tcggtgcaca c             231


<210> SEQ ID NO 46
<211> LENGTH: 371
<212> TYPE: DNA
<213> ORGANISM: Homo sapien

<400> SEQUENCE: 46

cccgggcagg tctgtgtaac atgccaaggc tttgcacttt ctgcagagca gtttttttatt     60

ttccttatca ggtacaggtt ttggtttttc ttgactatct ctgatgaatt tttcatgagt    120

ctgtatatgc agaatctttt ccctaaatac tgcttcgtcc catgtctgaa ggcgtaaaat    180

aaagtcattc atcatttttt ctttgtacat gtttatttgt tctttttcaa ttacaccaag    240

cattactagt cagaaggaag cacttgctac ctcttgctct tcctctgcct ctggtttgga    300

tcattttgat gacattgccc acattactca tgaaggatga caagattgca ctgtgcaatg    360

tcaattgcct t                                                         371


<210> SEQ ID NO 47
<211> LENGTH: 261
<212> TYPE: DNA
<213> ORGANISM: Homo sapien

<400> SEQUENCE: 47

gccctgtttt tatacacttc acatttgcag aaatataatg atgccctcat tatcagtgag     60

catgcacgaa tgaaagatgc tctggattac ttgaaagact tcttcagcaa tgtccgagca    120

gcaggattcg atgagattga gcaagatctt actcagagat ttgaagaaaa gctgcaggaa    180

ctagaaagtg tttccaggga tcccagcaat gagaatccta aacttgaaga cctctgcttc    240

atcttacaag aagagtacca c                                              261


<210> SEQ ID NO 48
<211> LENGTH: 701
<212> TYPE: DNA
<213> ORGANISM: Homo sapien

<400> SEQUENCE: 48

cgagcggccc ccgggcaggt ccaattagta caagtctcat gatataatca ctgcctgcat     60

acatatgcac agatccagtt agtgagtttg tcaagcttaa tctaattggt taagtctcaa    120

agagattatt attcttgatg tttgctttgt attggctaac aaatgtgcag aggtaataca    180

tatgtgatgt ccgatgtctc tgtctttttt tttgtcttta aaaaataatt ggcagcaact    240
```

-continued

```
gtatttgaat aaaatgattt cttagtatga ttgtaccgta atgaatgaaa gtggaacatg    300

tttctttttg aaagggagag aattgaccat ttattattgt gatgtttaag ttataactta    360

ttgagcactt ttagtagtga taactgtttt taaacttgcc taataccttt cttgggtatt    420

gtttgtaatg tgacttattt aacccccttt tttgtttgtt taagttgctg ctttaggtta    480

acagcgtgtt ttagaagatt taaatttttt tcctgtctgc acaattagtt attcagagca    540

agagggcctg attttataga agccccttga aaagaggtcc agatgagagc agagatacag    600

tgagaaatta tgtgatctgt gtgttgtggg aagagaattt tcaatatgta actacggagc    660

tgtagtgcca ttagaaactg tgaatttcca aataaatttg a                        701
```

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat     60

tttatgggcg ggtgccaaat actgctgtga atctatttgt atagtatcca tgaatgaatt    120

tatggaaata gatatttgtg cagctcaatt tatgcagaga ttaaatgaca tcataatact    180

ggatgaaaac ttgcatagaa ttctgattaa atagtgggtc tgtttcacat gtgcagtttg    240

aagtatttaa attaaccact cctttcacag                                     270
```

<210> SEQ ID NO 50
<211> LENGTH: 271
<212> TYPE: DNA
<213> ORGANISM: Homo sapien

<400> SEQUENCE: 50

```
atgcatttat ccatatgaac ttgattattc tgaattactg actataaaaa ggctattgtg     60

aaagatatca cactttgaaa cagcaaatga attttcaatt ttacatttaa ttataagacc    120

acaataaaaa gttgaacatg cgcatatcta tgcatttcac agaagattag taaaactgat    180

ggcaacttca gaattatttc atgaagggta caaacagtct ttaccacaat tttcccatgg    240

tcttatcctt caaaataaaa ttccacacac t                                   271
```

<210> SEQ ID NO 51
<211> LENGTH: 241
<212> TYPE: DNA
<213> ORGANISM: Homo sapien

<400> SEQUENCE: 51

```
tggtcgcggc cgaggtgtga ggagatgaac tttgtgttaa tggggggcac tttaaatcga     60

aatggcttat ccccaccgcc atgtaagtta ccatgcctgt ctcctccctc ctacacattt    120

ccagctcctg ctgcagttat tcctacagaa gctgccattt accagccctc tgtgattttg    180

aatccacgag cactgcaggc cctccacagc gttactaccc agcaggcact cagctcttca    240

t                                                                    241
```

<210> SEQ ID NO 52
<211> LENGTH: 271
<212> TYPE: DNA
<213> ORGANISM: Homo sapien

<400> SEQUENCE: 52

```
tccaagactt aaaacttagg aaacacctat gatgccactt taactggaag taatggagac     60
```

-continued

```
atctgattcc aaattcacat tttaaatgcc tatttgcaat cagcaaagag ccaggtatgc    120

tgcatgctgc ttgctgtaag ttacgatttg gcttcactag ctcaaatttt ttcactccac    180

caaaagataa ggcacaggcc cgtttgtcca atcaagtttg ctgaaaatac tgcagcctga    240

gtgtagacaa acttcccctg aatttgctag a                                   271


<210> SEQ ID NO 53
<211> LENGTH: 493
<212> TYPE: DNA
<213> ORGANISM: Homo sapien

<400> SEQUENCE: 53

ttagcgtggt cgcggtccga ggtctggcct gactagctca ctctgaagag tgtctttcac     60

atggattaac caaaaaatgc attactgcct ttggcacact gtcttgaata ttctttctga    120

caatgagaaa atatgattta atggagtcgt tcaataacct cacaatctcg ctgttccgag    180

cagatagttt tcgtgccaac aggaactggc acatctagca ggttcacggc atgacctttt    240

tgtggactgg ctggcataat tggaatgggt tttgattttt cttctgctaa taactcttca    300

agcttttgaa gttttcaagc attcctctcc agttgcctgt ggttggttct tgaacaccat    360

ctccaacccc accacctcca gatgcaacct tgtctcgtga tacagacctg cccgggcggc    420

cctcaagggc gaattctgca gatatccatc acactggcgg ccgctcgagc atgcatctag    480

agggcccaat tcg                                                       493


<210> SEQ ID NO 54
<211> LENGTH: 321
<212> TYPE: DNA
<213> ORGANISM: Homo sapien

<400> SEQUENCE: 54

cgtggtcgcg gccgaggtct gtttgcttgt tggtgtgagt ttttcttctg gagactttgt     60

actgaatgtc aataaactct gtgattttgt taggaagtaa aactgggatc tatttagcca    120

ctggtaagct tctgaggtga aggattcagg gacatctcgt ggaacaaaca ctccccactg    180

gactttctct ctggagatac ccttttgaat atacaatggc cttggctcac taggtttaaa    240

tacaaacaag tctgaaaccc actgaagact gagagattgc agcaatattc tctgaattag    300

gatcgggttc cataactcta a                                              321


<210> SEQ ID NO 55
<211> LENGTH: 281
<212> TYPE: DNA
<213> ORGANISM: Homo sapien

<400> SEQUENCE: 55

ttgcaaatga aactgtggat gtataataag aaaacacaag ggtttattct taacactaaa     60

attaacatgc cacacgaaga ctgcattaca gctctctgtt tctgtaatgc agaaaaatct    120

gaacagccca ccttggttac agctagcaaa gatggttact tcaaagtatg gatattaaca    180

gatgactctg acatatacaa aaaagctgtt ggctggacct gtgactttgt tggtagttat    240

cacaagtatc aagcaactaa ctgttgtttc tccgaagatg g                        281


<210> SEQ ID NO 56
<211> LENGTH: 612
<212> TYPE: DNA
<213> ORGANISM: Homo sapien
```

<400> SEQUENCE: 56
gcgtggtcgc ggccgaggtc ctgtccgggg gcactgagaa ctccctctgg aattcttggg 60
gggtgttggg gagagactgt gggcctggag ataaaacttg tctcctctac caccaccctg 120
taccctagcc tgcacctgtc ctcatctctg caaagttcag cttccttccc caggtctctg 180
tgccactctg tcttggatgc tctggggagc tcatgggtgg aggagtctcc accagaggga 240
ggctcagggg actggttggg ccagggatga atatttgagg gataaaaatt gtgtaagagc 300
caaagaattg gtagtagggg gagaacagag aggagctggg ctatgggaaa tgatttgaat 360
aatggagctg ggaatatggc tggatatctg gtactaaaaa agggtcttta agaacctact 420
tcctaatctc ttccccaatc caaaccatag ctgtctgtcc agtgctctct tcctgcctcc 480
agctctgccc caggctcctc ctagactctg tccctgggct agggcagggg aggagggaga 540
gcagggttgg gggagaggct gaggagagtg tgacatgtgg ggagaggacc agacctgccc 600
gggcggccgt cg 612

<210> SEQ ID NO 57
<211> LENGTH: 363
<212> TYPE: DNA
<213> ORGANISM: Homo sapien

<400> SEQUENCE: 57
gtcgcggccg aggtcctgag cgtcacccta gttctgcccc tttttagctg tgtagacttg 60
gacaagacat ttgacttccc tttctccttg tctataaaat gtggacagtg gacgtctgtc 120
acccaagaga gttgtgggag acaagatcac agctatgagc acctcgcacg gtgtccagga 180
tgcacagcac aatccatgat gcgttttctc cccttacgca ctttgaaacc catgctagaa 240
aagtgaatac atctgactgt gctccactcc aacctccagc gtggatgtcc ctgtctgggc 300 ccttttctg tttttattc tatgttcagc accactggca ccaaatacat tttaattcac 360
cga 363

<210> SEQ ID NO 58
<211> LENGTH: 750
<212> TYPE: DNA
<213> ORGANISM: Homo sapien

<400> SEQUENCE: 58
cgtggtcgcg gccgaggtct aattccacct gactggcaga acctgcgccc ctcgcctaac 60
ctgcgccctt ctcccaactc gcgtgcctca cagaacccag gtgctgcaca gccccgagat 120
gtggcccttc ttcaggaaag agcaaataag ttggtccaag tacttgatgc ttaaggaata 180
cacaaaggtg cccatcaagc gctcagaaat gctgagagat atcatccgtg aatacactga 240
tgtttatcca gaaatcattg aacgtgcatg ctttgtccta gagaagaaat ttgggattca 300
actgaaagaa attgacaaag aagaacacct gtatattctc atcagtaccc ccgagtccct 360
ggctggcata ctgggaacga ccaaagacac acccaagctc ggtctcttct tggtgattct 420
gggtgtcatc ttcatgaatg gcaaccgtgc cagtgaggct gtcttttggg aggcactacg 480
caagatggga ctgcgtcctg ggtgagaca tcccctccct tggagatcta aggaaacttc 540
tcacctatga gtttgtaaag cagaaatacc tggactacag acgagtgccc aacagcaacc 600
ccccggagta tgagttcctc tggggcctcc gtccctacca tgagactagc aagatgaaaa 660
tgctgagatt cattgcagag gttcagaaaa gagaccctcg tgactggact gcacagttca 720
tggaggctgc agatgaggac ctgcccgggc 750

<210> SEQ ID NO 59
<211> LENGTH: 505
<212> TYPE: DNA
<213> ORGANISM: Homo sapien

<400> SEQUENCE: 59

```
tggccgcccg ggcaggtcca gtctacaagc agagcactct catggggagc accagatgag     60
ttccagccgc agttctttta taagctttaa gtgcctcatg aagacgcgag gatctcttcc    120
aagtgcaacc tggtcacatc agggcacatt cagcagcaga agtctgtttc cagtatagtc    180
cttggtatgg ctaaattcca ctgtcccttt ctcagcagtc aataatccat gataaattct    240
gtacaacact gtagtcaata acagcagcac cagacagcat attaattctt ttaccataaa    300
tttgtgtgta attataatgt tctatgtgtg gtgttatcaa aagaatcact gtgtctctaa    360
atatcatata tgtatgtctg gataaataca ttgctgtaca acatctccaa catgcaggtc    420
atgctctaag acttggggat atagagtaat acatgtttcg tggacctcgg ccgcgaccac    480
gctaagggcg aattctgcag atatc                                          505
```

<210> SEQ ID NO 60
<211> LENGTH: 520
<212> TYPE: DNA
<213> ORGANISM: Homo sapien

<400> SEQUENCE: 60

```
cgtggtcgcg gccgaggtcc tcaggacaag gaaacaggta tcagcatgat ggtagcagaa     60
accttatcac caaggtgcag gagctgactt cttccaaaga gttgtggttc cgggcagcgg    120
tcattgcctg cccttgctgg agggctgatt ttagtgttgc ttattatgtt ggccctgagg    180
atgcttcgaa gtgaaaataa gaggctgcag gatcagcggc aacagatgct ctcccgtttg    240
cactacagct ttcacggaca ccattccaaa aaggggcagg ttgcaaagtt agacttggaa    300
tgcatggtgc cggtcagtgg gcacgagaac tgctgtctga cctgtgataa aatgagacaa    360
gcagacctca gcaacgataa gatcctctcg cttgttcact ggggcatgta cagtgggcac    420
gggaagctgg aattcgtatg acggagtctt atctgaacta cacttactga acagcttgaa    480
ggacctgccc gggcggccgc tcgaaagggg cgaattctgc                          520
```

<210> SEQ ID NO 61
<211> LENGTH: 447
<212> TYPE: DNA
<213> ORGANISM: Homo sapien

<400> SEQUENCE: 61

```
agagaggtgt ttttattctt tggggacaaa gccgggttct gtgggtgtag gattctccag     60
gttctccagg ctgtagggcc cagaggctta atcagaattt tcagacaaaa ctggaacctt    120
tctttttttcc cgttggttta tttgtagtcc ttgggcaaac caatgtcttt gttcgaaaga    180
gggaaaataa tccaaacgtt tttcttttaa cttttttttt aggttcaggg gcacatgtgt    240
aggcttgcta tataggtaaa ttgcatgtca ccagggtttg ttgtacagat tatttcatca    300
tccagataaa aagcatagta ccagataggt agttttttga tcctcaccct ccttccatgc    360
tccgacctca ggtaggcccc agtgtctgac ctgcccggcg gcccgctcga aagggccaat    420
tctgcagata tccatcacac tggccgg                                        447
```

<210> SEQ ID NO 62

<211> LENGTH: 83
<212> TYPE: PRT
<213> ORGANISM: Homo sapien

<400> SEQUENCE: 62

```
Lys Lys Val Leu Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
            20                  25                  30

Ser Asp Glu Leu Ala Ser Gly Phe Phe Val Phe Pro Tyr Pro Tyr Pro
        35                  40                  45

Phe Arg Pro Leu Pro Pro Ile Pro Phe Pro Arg Phe Pro Trp Phe Arg
    50                  55                  60

Arg Asn Phe Pro Ile Pro Ile Pro Ser Ala Pro Thr Thr Pro Leu Pro
65                  70                  75                  80

Ser Glu Lys
```

<210> SEQ ID NO 63
<211> LENGTH: 683
<212> TYPE: DNA
<213> ORGANISM: Homo sapien

<400> SEQUENCE: 63

```
acaaagattg gtagctttta tattttttta aaaatgctat actaagagaa aaaacaaaag      60

accacaacaa tattccaaat tataggttga gagaatgtga ctatgaagaa agtattctaa     120

ccaactaaaa aaaatattga aaccactttt gattgaagca aaatgaataa tgctagattt     180

aaaaacagtg tgaaatcaca ctttggtctg taaacatatt tagctttgct tttcattcag     240

atgtatacat aaacttattt aaaatgtcat ttaagtgaac cattccaagg cataataaaa     300

aaagwggtag caaatgaaaa ttaaagcatt tattttggta gttcttcaat aatgatrcga     360

gaaactgaat tccatccagt agaagcatct ccttttgggt aatctgaaca agtrccaacc     420

cagatagcaa catccactaa tccagcacca attccttcac aaagtccttc cacagaagaa     480

gtgcgatgaa tattaattgt tgaattcatt tcagggcttc cttggtccaa ataaattata     540

gcttcaatgg gaagaggtcc tgaacattca gctccattga atgtgaaata ccaacgctga     600

cagcatgcat ttctgcattt tagccgaagt gagccactga acaaaactct tagagcacta     660

tttgaacgca tctttgtaaa tgt                                             683
```

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64

```
ctgttcattt gtccgccagc tcctggactg gatgtgtgaa aggcatcaca tttccatttt      60

cctccgtgta aatgttttat gtgttcgcct actgatccca ttcgttgctt ctattgtaaa     120

tatttgtcat ttgtatttat tatctctgtg ttttccccct aaggcataaa atggtttact     180

gtgttcattt gaacccattt actgatctct gttgtatatt tttcatgcca ctgctttgtt     240

ttctcctcag aagtcgggta gatagcattt ctatcccatc cctcacgtta ttggaagcat     300

gcaacagtat ttattgctca gggtcttctg cttaaaactg aggaaggtcc acattcctgc     360
```

-continued

```
aagcattgat tgagacattt gcacaatcta aaatgtaagc aaagtaagtc attaaaaata    420

caccctctac ttgggcttta tactgcatac aaatttactc atgagccttc ctttgaggaa    480

ggatgtggat ctccaaataa agatttagtg tttattttga gctctgcatc ttancaagat    540

gatctgaaca cctctccttt gtatcaataa atagccctgt tattctgaag tgagaggacc    600

aagtatagta aaatgctgac atctaaaact aaataaatag aaaacaccag gccagaacta    660

tagtcatact cacacaaagg gagaaattta aactcgaacc aagcaaaagg cttcacggaa    720

atagcatgga aaaacaatgc ttccagtgg                                      749
```

<210> SEQ ID NO 65
<211> LENGTH: 612
<212> TYPE: DNA
<213> ORGANISM: Homo sapien

<400> SEQUENCE: 65

```
acagcagcag tagatggctg caacaacctt cctcctaccc cagcccagaa aatatttctg     60

ccccacccca ggatccggga ccaaaataaa gagcaagcag gccccccttca ctgaggtgct   120

gggtagggct cagtgccaca ttactgtgct ttgagaaaga ggaaggggat ttgtttggca    180

ctttaaaaat agaggagtaa gcaggactgg agaggccaga gaagatacca aaattggcag    240

ggagagacca tttggcgcca gtcccctagg agatgggagg agggagatag gtatgagggt    300

aggcgctaag aagagtagga ggggtccact ccaagtggca gggtgctgaa atgggctagg    360

accaacagga cactgactct aggtttatga cctgtccata cccgttccac agcagctggg    420

tgggagaaat caccattttg tgacttctaa taaaataatg ggtctaggca acagttttca    480

atggatgcta aaacgattag gtgaaaagtt gatggagaat tttaattcag gggaattagg    540

ctgataccat ctgaaaccat ttggcatcat taaaaatgtg acaacctggt ggctgccagg    600

gaggaagggg ag                                                        612
```

<210> SEQ ID NO 66
<211> LENGTH: 703
<212> TYPE: DNA
<213> ORGANISM: Homo sapien

<400> SEQUENCE: 66

```
tagcgtggtc gcggccgagg tacattgatg ggctggagag cagggttggc agcctgttct     60

gcacagaacc aagaattaca gaaaaaagtc caggagctgg agaggcacaa catctccttg    120

gtagctcagc tccgccagct gcagacgcta attgctcaaa cttccaacaa agctgcccag    180

accagcactt gtgttttgat tcttcttttt tccctggctc tcatcatcct gcccagcttc    240

agtccattcc agagtcgacc agaagctggg tctgaggatt accagcctca cggagtgact    300

tccagaaata tcctgaccca caaggacgta acagaaaatc tggagaccca agtggtagag    360

tccagactga gggagccacc tggagccaag gatgcaaatg gctcaacaag gacactgctt    420

gagaagatgg gagggaagcc aagacccagt gggcgcatcc ggtccgtgct gcatgcagat    480

gagatgtgag ctggaacaga ccttcctggc ccacttcctg atcacaagga atcctgggct    540

tccttatggc tttgcttccc actgggattc ctacttaggt gtctgccctc aggggtccaa    600

atcacttcag gacaccccaa gagatgtcct ttagtctctg cctgaggcct agtctgcatt    660

tgtttgcata tatgagaggg tacctgcccg ggcggccgct cga                      703
```

<210> SEQ ID NO 67
<211> LENGTH: 1022

<212> TYPE: DNA
<213> ORGANISM: Homo sapien

<400> SEQUENCE: 67

```
cttgagaaag caggattgtt ttaagttcca agatttaaca aacttactgt tcagcatcat     60
attcaagcct aaaaggaaga taggattttc aagatatatt tccaacttct ttaacatggc    120
accatggatg aactgtttct cagcactgtg ctgcttcact tggaattaag gatgaattgg    180
gaggagacag tatgacatag gtgggtaggt tgggtggtga ggggaaccag ttctaatagt    240
cctcaactcc actccagctg ttcctgttcc acacggtcca ctgagctggc ccagtccctt    300
tcactcagtg tgtcaccaaa ggcagcttca aggctcaatg gcaagagacc acctataacc    360
tcttcacctt ctgctgcctc tttctgctgc cactgactgc catggccatc tgctatagcc    420
gcattgtcct cagtgtgtcc aggccccaga caaggaaggg gagccatggt gagactccaa    480
ttcccaggcc ttaatcctta accctagacc tgttgcctct agcatcattt atttatctac    540
ctacctaata gctatctacc agtcattaaa ccatggtgag attctaacca tgtctagcac    600
ctgatgctag agataatttt gttgaatccc ttcaattata aacagctgag ttagctggac    660
aaggactagg gaggcaatca gtattattta ttcttgaaca ccatcaagtc tagacttggt    720
ggcttcatat ttctatcata atccctgggg gtaagaaatc atatagcccc aggttgggaa    780
ggggaaaacg gtttgcaaca ttctcctcct tgtaggaggc gagctctgtc tcactagcta    840
tgcccctcca tcaattcacc ctatactcag atcagaagct gagtgtctga attacagtat    900
attttctaaa ttcctagccc ctgctggtga atttgccctc ccccgctcct ttgacaattg    960
tccccgtgtt cgtctccggg ccctgagact ggccctgctt atcttgctga ccttcatcct   1020
ct                                                                  1022
```

<210> SEQ ID NO 68
<211> LENGTH: 449
<212> TYPE: DNA
<213> ORGANISM: Homo sapien

<400> SEQUENCE: 68

```
ccagatccat tttcagtggt ctggatttct ttttattttc ttttcaactt gaaagaaact     60
ggacattagg ccactatgtg ttgttactgc cactagtgtt caagtgcctc ttgttttccc    120
agagatttcc tgggtctgcc agaggcccag acaggctcac tcaagctctt taactgaaaa    180
gcaacaagcc actccaggac aaggttcaaa atggttacaa cagcctctac ctgtcgcccc    240
agggagaaag gggtagtgat acaagtctca tagccagaga tggttttcca ctccttctag    300
atattcccaa aaagaggctg agacaggagg ttattttcaa ttttattttg gaattaaata    360
ctttttttccc tttattactg ttgtagtccc tcacttggat atacctctgt tttcacgata    420
gaaataaggg aggtctagag cttctattc                                     449
```

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69

```
gcccttagcg tgggtcgcgg cncgangtct ggagcntatg tgatncctat ggtncncagg     60
```

-continued

```
cnnatactgc tantctcatt tattctcctg cnacctantc ctctnctctg gaatcacacc    120

attattgcct gttaacactg gactgtgagt accangcaat taatttgcac caanaaagtt    180

gagggtatta tcanatattg caatctgtac agagggaaga tgatttcaat ttgatttcaa    240

cttaaccttc atctttgtct gttaacacta atagagggtg tctaataaaa tggcaaattt    300

gngatctcat tnggtataac tacactcttt ttcacagatg tgatgactga atttccanca    360

acctgcccgg gcggncgntc naagggc                                        387


<210> SEQ ID NO 70
<211> LENGTH: 836
<212> TYPE: DNA
<213> ORGANISM: Homo sapien

<400> SEQUENCE: 70

tattccattt acaaaataaa ttcagccctg cactttcttt agatgccttg atttccagaa     60

tggagcttag tgctactgaa taccctggcc acagagccac ctcaggatat tcttttctcc    120

accctagttt atttatttat agatatctgt ttacaaagtc tgtagtaaat cctgatgctg    180

accatctgaa atgtactttt tttctgaatg ctgtttcaat ctaaaatagc agcttttgag    240

aaaacaatga tgtaaattcc ttatgataaa aggatgattc tatatattct ttaatgatat    300

taaatatgcc gaagccaagc acacagtctt tctaaagtgt gtgtatgttt gtgtgaatgt    360

gaatgatact gatcttatat ctgttaaaag ttgttttaaa aagctgtggc atcccattgt    420

tcatatttgc caagtcttct gtaaagatgt ctaggacgaa atattttatg tgctaatgca    480

tgtatttgta aaccagattt gtttaccact caaaattaac ttgttttctt catccaaaaa    540

agtttatttc ttccacgtac ttaaattttc tgtgtgggta taatatagct ttctaatttt    600

tttctttcac aaaggcaggt tcaaaattct gttgaaagaa aaatgctttc tgaaactgag    660

gtataacacc agagcttgct gtttaaagga ttatatgatg tacatcagtt ctataaatgt    720

gctcagcagt ttaacatgtg aatcctgttt taaagtgctc agatttcaac tgtgtaagcc    780

attgatataa cgctgtaatt aaaaatgttt atatgaaaaa aaaaaaaaaa aaaaaa        836


<210> SEQ ID NO 71
<211> LENGTH: 618
<212> TYPE: DNA
<213> ORGANISM: Homo sapien

<400> SEQUENCE: 71

gttgcagtga gctcaagtgt tgggtgtatc agctcaaaac accatgtgat gccaatcatc     60

tccacaggag caatttgttt acctttttt tctgatgctt tactaacttc atcttttaga    120

tttaaatcat tagtagatcc tagaggagcc agtttcagaa aatatagatt ctagttcagc    180

accacccgta gttgtgcatt gaaataatta tcattatgat tatgtatcag agcttctggt    240

tttctcattc tttattcatt tattcaacaa ccacgtgaca aacactggaa ttacaggatg    300

aagatgagat aatccgctcc ttggcagtgt tatactatta tataacctga aaaaacaaac    360

aggtaatttt cacacaaagt aatagatatc atgacacatt taaaataggg cactactgga    420

acacacagat aggacatcca ggttttgggt caatattgta gactttttgg tggatgagat    480

atgcaggttg atrccagaag gacaacaaaa acatatgtca gatagaaggg aggagcaaat    540

gccaagagct ggagctgagg aagatcactg tgaaattcta tgtagtctag ttggctggat    600

gctagagcaa agaggtgg                                                  618
```

<210> SEQ ID NO 72
<211> LENGTH: 806
<212> TYPE: DNA
<213> ORGANISM: Homo sapien

<400> SEQUENCE: 72

```
tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300

agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctcccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                         806
```

<210> SEQ ID NO 73
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 73

```
actctggtaa gcttgttgtt gtccaagtga agctccctca gatgaggcgt gttggccana     60

gagccattgt caacagcaga gatgctgttg aaactcaatc ccaacttagc caaattattc    120

agtcctttca ggctagctgc atcaactctg ctgattttgt tgccatcaag atgtaattcc    180

gtaagggaag gaggaagacc ttgaggaatg ctggygatat tggyatcagc aatgcggatg    240

tasgaagagc ttcttcmttc cctggaaagc cccattttca atyccttgag ctcttcakcg    300

g                                                                    301
```

<210> SEQ ID NO 74
<211> LENGTH: 401
<212> TYPE: DNA
<213> ORGANISM: Homo sapien

<400> SEQUENCE: 74

```
agtttacatg atccctgtaa cagccatggt ctcaaactca gatgcttcct ccatctgcca     60

agtgtgttct ggatacagag cacatcgtgg cttctggggt cacactcagc ttaggctgtg    120

ggtccacaga gcactcatct ggctgggcta tggtggtggt ggctctactc aagaagcaaa    180

gcagttacca gcacattcaa acagtgtatt gaacatcttt taaatatcaa agtgagaaac    240

aagaaggcaa cataataatg ttatcagaaa gatgttagga agtaaggaca gctgtgtaaa    300

gcttgaggct gaaaagtagc ttgccagctt catttctttg gtttcttggg tagtgggccg    360
```

-continued

```
ccggaacagc aagatgtgag gttctggttc atggatcata t                 401


<210> SEQ ID NO 75
<211> LENGTH: 612
<212> TYPE: DNA
<213> ORGANISM: Homo sapien

<400> SEQUENCE: 75

ttatttttca atttttattt tggttttctt acaaaggttg acattttcca taacaggtgt     60

aagagtgttg aaaaaaaaat tcaaattttt ggggagcgag ggaaggagtt aatgaaactg    120

tattgcacaa tgctctgatc aatccttctt tttctctttt gcccacaatt taagcaagta    180

gatgtgcaga agaaatggaa ggattcagct ttcagttaaa aaagaagaag aagaaatggc    240

aaagagaaag ttttttcaaa tttctttctt ttttaattta gattgagttc atttatttga    300

aacagactgg gccaatgtcc acaaagaatt cctggtcagc accaccgatg tccaaaggtg    360

caatatcaag gaagggcagg cgtgatggct tatttgtttt gtattcaatg attgtctttc    420

cccattcatt tgtcttttta gagcagccat ctacaagaac agtgtaagtg aacctgctgt    480

tgccctcagc aacaagttca acatcattag agccctgtag aatgacagcc tttttcaggt    540

tgccagtctc ctcatccatg tatgcaatgc tgttcttgca gtggtaggtg atgttctgag    600

aggcatagtt gg                                                        612


<210> SEQ ID NO 76
<211> LENGTH: 844
<212> TYPE: DNA
<213> ORGANISM: Homo sapien

<400> SEQUENCE: 76

ggctttcgag cggccgcccg ggcaggtctg atggttctcg taaaaacccc gctagaaact     60

gcagagacct gaaattctgc catcctgaac tcaagagtgg agaatactgg gttgacccta    120

accaaggatg caaattggat gctatcaagg tattctgtaa tatggaaact ggggaaacat    180

gcataagtgc caatcctttg aatgttccac ggaaacactg gtggacagat tctagtgctg    240

agaagaaaca cgtttggttt ggagagtcca tggatggtgg ttttcagttt agctacggca    300

atcctgaact tcctgaagat gtccttgatg tgcagcykgc attccttcga cttctctcca    360

gccgagcttc ccagaacatc acatatcact gcaaaaatag cattgcatac atggatcagg    420

ccagtggaaa tgtaaagaag gccctgaagc tgatggggtc aaatgaaggt gaattcaagg    480

ctgaaggaaa tagcaaattc acctacacag ttctggagga tggttgcacg aaacacactg    540

gggaatggag caaaacagtc tttgaatatc gaacacgcaa tgctgttcct tgacattgca    600

ccaccaatgt ccagaggtgc aatgtcaagg aacggcaggc gagatggctt atttgttttg    660

tattcaatga ttgtcttgcc ccattcattt gtctttttgg agcagccatc gactaggaca    720

gagtaggtga acctgctgtt gccctcagca acaagttcca catcgttgga accctgcaga    780

agcacagcct tgttcaarct gcccgtctcc tcatccagat acctcggccg cgaccacgct    840

aatc                                                                 844


<210> SEQ ID NO 77
<211> LENGTH: 314
<212> TYPE: DNA
<213> ORGANISM: Homo sapien

<400> SEQUENCE: 77

ccagtcctcc acttggcctg atgagagtgg ggagtggcaa gggacgtttc tcctgcaata     60
```

```
gacacttaga tttctctctt gtgggaagaa accacctgtc catccactga ctcttctaca    120

ttgatgtgga aattgctgct gctaccacca cctcctgaag aggcttccct gatgccaatg    180

ccagccatcc tggcatcctg gccctcgagc aggctgcggt aagtagcgat ctcctgctcc    240

agccgtgtct ttatgtcaag cagcatcttg tactcctggt tctgagcctc catctcgcat    300

cggagctcac tcag                                                      314


<210> SEQ ID NO 78
<211> LENGTH: 548
<212> TYPE: DNA
<213> ORGANISM: Homo sapien

<400> SEQUENCE: 78

accaagagcc aagtgttaca caggatattt taaaaataaa atgtttttgg aatcctcacc     60

tcccatgcta tcttctaaga taactacaaa tattcttcaa agatttaact gagttctgcc    120

aaggacctcc caggactcta tccagaatga ttattgtaaa gctttacaaa tcccaccttg    180

gccctagcga taattaggaa atcacaggca aacctcctct ctcggagacc aatgaccagg    240

ccaatcagtc tgcacattgg ttttgttaga tactttgtgg agaaaaacaa aggctcgtga    300

tagtgcagct ctgtgcctac agagagcctc ccttttggtt ctgaaattgc tgatgtgaca    360

gagacaaagc tgctatgggt ctaaaacctt caataaagta actaatgaca ctcaaggtcc    420

tgggactctg agacagacgg tggtaaaacc cacagctgcg attcacattt ccaatttatt    480

ttgagctctt tctgaagctg ttgcttccta cctgagaatt cccatttaga gagctgcaca    540

gcacagtc                                                             548


<210> SEQ ID NO 79
<211> LENGTH: 646
<212> TYPE: DNA
<213> ORGANISM: Homo sapien

<400> SEQUENCE: 79

accccgtcac tatgtgaata aaggcagcta gaaaatggac tcaattctgc aagccttcat     60

ggcaacagcc catattaaga cttctagaac aagttaaaaa aaatcttcca tttccatcca    120

tgcatgggaa aagggcttta gtatagttta ggatggatgt gtgtataata ataaaatgat    180

aagatatgca tagtggggga ataaagcctc agagtccttc cagtatgggg aatccattgt    240

atcttagaac cgagggattt gtttagattg ttgatctact aatttttttc ttcacttata    300

tttgaatttt caatgatagg acttattgga aattggggat aattctgttg tggtattaaa    360

taatattcat tttttaaaaa ctcatcttgg tattgagtta gtgcattgac ttccaatgaa    420

ttgacataag cccatatttc attttaacca gaaacaaaaa ctagaaaatg ttactcccta    480

aataggcaac aatgtatttt ataagcactg cagagattta gtaaaaaaca tgtatagtta    540

ctttagaaac aacttctgac acttgagggt tacccaatgg tctccttccc attctttata    600

tgaggtaaat gcaaaccagg gagccaccga ataaacagcc ctgagt                   646


<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G
```

<400> SEQUENCE: 80
gtctgaatga gcttcnctgc gagatggganc ancataaccc agaantccaa aancntanng 60
aacgnnaaaa cccgntngaa caagnaaacn gcaactnacg gccgcctgnt gnagggcgag 120
gacgcccacc tctcctcctc ccagttctcc tctggatcgc agncatccan agatgtgacc 180
tcttccagcc gccaaatccg caccaaggtc atggatgtgc acgatggcaa ggtgggtgtc 240
cacccacgaa caggtccttc gcaccaagaa ctgagg 276

<210> SEQ ID NO 81
<211> LENGTH: 647
<212> TYPE: DNA
<213> ORGANISM: Homo sapien

<400> SEQUENCE: 81
gtcctgcctt tcatcttttc tttaaaaaaa ataaatgttt acaaaacatt tccctcagat 60
tttaaaattc atggaagtaa taaacagtaa taaaatatgg atactatgaa aactgacaca 120
cagaaaaaca taaccataaa atattgttcc aggatacaga tattaattaa gagtgacttc 180
gttagcaaca cgtagacatt catacatatc cggtggaaga ctggtttctg agatgcgatt 240
gccatccaaa cgcaaatgct tgatcttgga gtaggrtaat ggccccagga tcttgcagaa 300
gctctttatg tcaaacttct caagttgatt gacctccagg taatagtttt caaggttttc 360
attgacagtt ggtatgtttt taagcttgtt ataggacaga tccagctcaa ccagggatga 420
cacattgaaa gaatttccag gtattccact atcagccagt tcgttgtgag ataaacgcag 480
atactgcaat gcattaaaac gcttgaaata ctcatcaggg atgttgctga tcttattgtt 540
gtctaagtag agagttagaa gagagacagg gagaccagaa ggcagtctgg ctatctgatt 600
gaagctcaag tcaaggtatt cgagtgattt aagaccttta aaagcag 647

<210> SEQ ID NO 82
<211> LENGTH: 878
<212> TYPE: DNA
<213> ORGANISM: Homo sapien

<400> SEQUENCE: 82
ccttctttcc ccactcaatt cttcctgccc tgttattaat taagatatct tcagcttgta 60
gtcagacaca atcagaatya cagaaaaatc ctgcctaagg caaagaaata taagacaaga 120
ctatgatatc aatgaatgtg ggttaagtaa tagatttcca gctaaattgg tctaaaaaag 180
aatattaagt gtggacagac ctatttcaaa ggagcttaat tgatctcact tgttttagtt 240
ctgatccagg gagatcaccc ctctaattat ttctgaactt ggttaataaa agtttataag 300
atttttatga agcagccact gtatgatatt ttaagcaaat atgttattta aaatattgat 360
ccttcccttg gaccaccttc atgttagttg ggtattataa ataagagata caaccatgaa 420
tatattatgt ttatacaaaa tcaatctgaa cacaattcat aaagatttct cttttatacc 480
ttcctcactg gccccctcca cctgcccata gtcaccaaat tctgttttaa atcaatgacc 540
taagatcaac aatgaagtat tttataaatg tatttatgct gctagactgt gggtcaaatg 600
tttccatttt caaattattt agaattctta tgagtttaaa atttgtaaat ttctaaatcc 660
aatcatgtaa aatgaaactg ttgctccatt ggagtagtct cccacctaaa tatcaagatg 720
gctatatgct aaaaagagaa aatatggtca agtctaaaat ggctaattgt cctatgatgc 780
tattatcata gactaatgac atttatcttc aaaacaccaa attgtcttta gaaaaattaa 840
tgtgattaca ggtagagaac ctcggccgcg accacgct 878

<210> SEQ ID NO 83
<211> LENGTH: 645
<212> TYPE: DNA
<213> ORGANISM: Homo sapien

<400> SEQUENCE: 83
acaaacattt tacaaaaaag aacattacca atatcagtgg cagtaagggc aagctgaaga 60
ataaatagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240
atacaagtgg aactcatcaa ataatttaaa cccaaggcga taacaacgct atttcccatc 300
taaactcatt taagccttca caatgtcgca atggattcag ttacttgcaa acgatcccgg 360
gttgtcatac agatacttgt ttttacacat aacgctgtgc catcccttcc ttcactgccc 420
cagtcaggtt tcctgttgtt ggaccgaaag ggatacattt ttagaaatgc ttccctcaag 480
acagaagtga gaaagaaagg agaccctgag gccaggatct attaaacctg gtgtgtgcgc 540
aaaagggagg gggaaggcag gaatttgaaa ggataaacgt ctcctttgcg ccgaggaatc 600
aggaagcgtg actcacttgg gtctgggacg ataccgaaat ccggt 645

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84
tctgatgtca atcacaactt gaaggatgcc aatgatgtac caatccaatg tgaaatctct 60
cctcttatct cctatgctgg agaaggatta gaaggttatg tggcagataa agaattccat 120
gcacctctaa tcatcgatga gaatggagtt catgggctgg tgaaaaatgg tatttgaacc 180
agataccaag ttttgtttgc cacgatagga atagctttta tttttgatag accaactgtg 240
aacctacaag acgtcttgga caactgaagn ttaaatatcc acangggttt attttgcttg 300
g 301

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85
agcgtgggtc gcggcncgan gtagagaacc gactgaaacg tttgagatga agaaagttct 60
cctcctgatc acagccatct tggcagtggc tgttggtttc ccagtctctc aagaccagga 120
acgagaaaaa agaagtatca gtgacagcga tgaattagct tcagggtttt ttgtgttccc 180
ttacccatat ccatttcgcc cacttccacc aattccattt ccaagatttc catggtttan 240
acgtaatttt cctattccaa tacctgaatc tgcccctaca actccccttc ctagcg 296

<210> SEQ ID NO 86

<211> LENGTH: 806
<212> TYPE: DNA
<213> ORGANISM: Homo sapien

<400> SEQUENCE: 86

```
tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300

agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctcccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                          806
```

<210> SEQ ID NO 87
<211> LENGTH: 620
<212> TYPE: DNA
<213> ORGANISM: Homo sapien

<400> SEQUENCE: 87

```
tttttgcatc agatctgaaa tgtctgagag taatagtttc tgttgaattt ttttttgttc     60

atttttctgc acagtccatt ctgtttttat tactatctag gcttgaaata tatagtttga    120

aattatgaca tccttcctct ttgttatttt cctcatgatt gctttggcta ttcaaagttt    180

attttagttt catgtaaatt tttgaattgt attttccatt attgtgaaaa tagtaccact    240

gcaattttaa taggaagttt attgaatcta tagattactt tggataatat ggcacttcaa    300

taatattcat gttttcaatt catagacaaa atattttaaa atttatttgt atcttttcta    360

atttttcctt tttttattgt aaagatttac ctccttggtt aatattttcc tcagaaattt    420

attatttaag gtatagtcaa taaaattttc ttcctctatt ttgtcagata gtttaagtgt    480

atgaaaccat agatatactt gtatgttaat tttatatttt gctaatttac tgagtgtatt    540

tattagttta gagaggtttt aatgtactgt ttatggtttt ttaaatataa gattacttat    600

tttttaaaaa aaaaaaaaaa                                                 620
```

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88

```
tagctgtgnt cagcaggccg aggttttttt tttttttgag atggagtctc gccctgtcac     60

ccaggctgga gtgcagtggc ctgatctcag ctcactgcaa gctccacctc ctggattcac    120
```

-continued

```
gctattctcc tgcctcagcc tcccaagtag ctgggactac aggcgcccgc caccacgccc    180

agctaattnt ttgnattttt agtacnagat gcggtttcat cgtgttagcc agcatggnct    240

cgatctcctg acctcgtgaa ctgcccgcct cggcctccca aagacctgcc cgggcnggcc    300

gctcgaaa                                                             308


<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89

agcggccgcc cgggcaggtc tgttaagtaa catacatatc accttaataa aaatcaagat     60

gaaatgtttt agaaactatt ttatcaaaag tggctctgat acaaagactt gtacatgatt    120

gttcacagca gcactattaa tgccaaaaag tagacaaaac ctaaatgtcc attaactgat    180

aagcaaaatg tggtatatcc atacaatgga atattatgta gcccacaaca tggcatggag    240

tactacaaca tggatgagcc tcaaaaacgt tatgctaaat gaaaaaagtc agatatagga    300

aaccacatgt catatgatcc catttatatg aaatagccag aaaaggcaag tcatagaaac    360

aagatagatc ggaaaatggg ttggaggact acaaatggca ccagggatct ttgaagttga    420

tggaaatggt ctaaaatcag actgtggntg tggttgaaca agtctgtaaa tttaccaaaa    480

tgcgttaata ca                                                        492


<210> SEQ ID NO 90
<211> LENGTH: 390
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90

tcgagcggcc gcccgggcag gtacaagctt tttttttttt tttttttttt ttttctaaca     60

gttctctgtt ttattgcaat acagcaaagt ctggttaata ttaagngata tcaacataaa    120

gtattggtga ggagtctttt gtgacatttt ttaccatccc accttaaata tttctgtgca    180

aaanaatcca catcattgtt tggtancana ggatctctta aaaagttccc taanacactg    240

agggcataaa accaaacaaa ataaaataag gagtgatagg ctaaagcagt atcttcccct    300

ccatccacat ttgncaagca ttatattcta accaaaaaat gatcacacca ggccatgcaa    360

aactgtccaa tattaccgag aaaaaaccct                                     390


<210> SEQ ID NO 91
<211> LENGTH: 192
<212> TYPE: DNA
<213> ORGANISM: Homo sapien

<400> SEQUENCE: 91

agcgtggtcg cggccgaggt ctgtcaatta atgctagtcc tcaggattta aaaaataatc     60

ttaactcaaa gtccaatgca aaaacattaa gttggtaatt actcttgatc ttgaattact    120

tccgttacga aagtccttca catttttcaa actaagctac tatatttaag gcctgcccgg    180
```

gcggccgctc ga 192

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92
agcgtggtcg cggccgaggt ctgacaacta acaaagaagc aaaaactggc atcttggaca 60
tcctagtatt acacttgcaa gcaattagaa cacaaggagg gccaaggaaa aagtttagct 120
ttgaatcact tccaaatcta ctgattttga ggttccgcag tagttctaac aaaacttttc 180
agacaatgtt aactttcgat taagaaagaa aaaaacccca aacatcttca ggaattccat 240
gccaggttca gtctcttcca gtgagcccgc ttgctaaaag tccacgtgca ccattaatta 300
gctgggctgg cagcaccatg taaaaagaag cctattcacc accaaccaca cagactagac 360
atgtaaagta ggatcaagta atggatgaca accatggtcg tggaatatgg tcaatgagag 420
tcagaaaagt acaggcacca gtacaagcag cagataacag aattgacggg ccaaaggata 480
aaaataggct tatttaaata ggatgctaca gaacacatnc acttctaatt ggaagctgct 540
ttacactggg tggcattgna ccatatgcat 570

<210> SEQ ID NO 93
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 93
tcgagcggcc gcccgggcag gtccaggttt ttatttagtt gtgtaatctt ggacaagtta 60
cctaactttt ttgagtctga atatatttaa tctgcaaaat gagaatcatg ataatacgtc 120
ataggcttaa ttaggaggat taaatgaaat aatttatagg tggtgccatg gttacataca 180
agtattagta gttaattctt ttcctttgtt tacttttata gtataggttg gatgaaggtt 240
ccagtatagg caaaaatact acttggggt aaagtagagt gtgatacttt atttgaaatg 300
ttccctgaat ctgatcttta ctttttgnta ctgctgcact acccaaatcc aaattttcat 360
cccaacattc ttggatttgt gggacagcng tagcagcttt tccaatataa tctatactac 420
atcttttctt actttggtgc tttttg 446

<210> SEQ ID NO 94
<211> LENGTH: 409
<212> TYPE: DNA
<213> ORGANISM: Homo sapien

<400> SEQUENCE: 94
cgagcggccg cccgggcagg tccatcagct cttctgctta gaatacgagg cagacagtgg 60
agaggtcaca tcagttatcg tctatcaggg tgatgaccca agaaaggtga gtgagaaggt 120
gtcggcacac acgcctctgg atccacccat gcgagaagcc ctcaagttgc gtatccagga 180
ggagattgca aagcgccaga gccaacactg accatgttga aggcgttctc tccaggctgg 240
attcactgca ctcggaagaa ttctgcccag ggaatttagt gtgggggtac caggaccagt 300

```
ttgtcttgat cttgagaccc ccagagctgc tgcatccata gggtgttgca ggactacacc    360

tggcctgcct tgcagtcatt ctttcttata tgttgaccca tttgcccaa                409


<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95

tcgagcggcc gcccgggcag gtcctacttg tttgcagctt ccacacactg cacctaccta     60

ctacctctct tccatgctta actgggttta gaaaggtgag ctatgcgtag aagaactact    120

tgggatattc aagtgctgta tttgaacgat aagcctatag ataacagtct gaagctgcaa    180

gggagacttt gttagtacac tactataaac aggtaaacta cctgtttgta cttgatatag    240

tgcatatgaa atgactgatt taatacaaaa ctacagaaca tgcaaaattt tttctgagat    300

gttaagtatt acttcagtgg agaacaaaac ttacttaacc tttcgctaat gcatgtagta    360

ccagaaagca aacatggttt tagcttcctt tactcaaaat atgaacatta agtggttgtg    420

aattttgtct gccaagtggt tcagaaaata cattataaat aacctaagtt aaaaaaaaga    480

aactgngaac                                                           490


<210> SEQ ID NO 96
<211> LENGTH: 223
<212> TYPE: DNA
<213> ORGANISM: Homo sapien

<400> SEQUENCE: 96

agcgtggtcg cggccgaggt ctggaagccc accctaggac ttgaatggca ccttgtcctt     60

tctctgccag taatgcaatc caacacaata tgctacaggg aaaacagaat ttccacggtg    120

ccgccctctg gtacaaggga aacagcacgc aaagcaaaag gccacagagg gctccctgag    180

aatccagtac aactaagcga ggacctgccc gggcggccgc tcg                      223


<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97

tcgagcggcc gcccgggcag gtctgtgcag gagacactga agtgggtagt gtccataatc     60

tttttagcct gttgctgaaa ttccagttgt actccttcaa accaaaatgc ttacaggatc    120

atgggaaagc ctcggttgca gaaatcaaga caggcaagtg ggaagataac tcggctttga    180

ggttaaacag atctgggttc aaagcatagt ttcactctct gtcttgtgaa gtgtcctggg    240

tgaagtcatt tcctctcttg aatttcagag aggatgaaaa tataaaaagt ataataacta    300

tcttcataat ctttgtgagg attaaagaag acgaagtgtg tgaaaagcta agcacagagc    360

aggcattcta caataagtag ttattatttt tggaaccatc ccgnccctag ccccagccca    420

attaccttct cttagnctct tcatatcgaa ngccgtaatc ttgaccttct cttgcnactg    480
```

```
gattggtgct ggttgatgcc caaacttccc gagatgctgt ctgggaa              527


<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98

tcgagcggcc gcccgggcag gtctggctcc catggccctt ggggtggcct gactctgtca     60

ctattcctaa aaccttctag gacatctgct ccaggaagaa ctttcaacac caaaattcat    120

ctcaatttta cagatgggaa aagtgattct gagaccagac cagggtcagg ccaaggtcat    180

ccagcatcag tggctgggct gagactgggc ccagggaacc ctgtctgctc ctctttttcc    240

cagagctgtg agttctctag ccaaggctgc actcttgagg gagagccagg aagcatagct    300

gaggccatga caacctcact cttcacctga aaatttaacc cgtggcagag gatccaggca    360

catataggct tcggagccaa acaggacctc ggccgcgacc acgctaagcc gaattccagc    420

acactggcgg ccgttactag tggatcccga gcttnggtac caagcttggc gtaatcatgg    480

gcatagctgg ttcctggggt gaaaatggta tccg                                514


<210> SEQ ID NO 99
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 99

tcgagcggcc gcccgggcag gtctgaagaa acaggtataa atttggcagc cagtaatttt     60

gacagggaag ttacagcttg catgacttta aatatgtaaa tttgaaaata ctgaatttcg    120

agtaatcatt gtgctttgtg ttgatctgaa aaatataaca ctggctgtcg aagaagcatg    180

ttcaaaaata tttaattcac ttcaaaatgt catacaaatt atggtggttt ctatgcaccc    240

ctaaagcttc aagtcattta gctcaggtac atactaaagt aatatattaa ttcttccagt    300

acagtggtgt ttcataccat tgacatttgc ataccctaga ataatttaag aaagacatgt    360

gtaatattca caatgttcag aaaagcaagc aaaaggtcaa ggaacctgct ttggttcttc    420

tggagatggn ctcatatcag cttcataaac attcattcta caaaatagta agctaaccat    480

ttgaacccca atttccagat taagcatatt ttctcataaa tnatgaagcc              530


<210> SEQ ID NO 100
<211> LENGTH: 529
<212> TYPE: DNA
<213> ORGANISM: Homo sapien

<400> SEQUENCE: 100

agcgtggtcg cggccgaggt ccaggcacgg tggcttatgt gtgtaatccc agcacttggg     60

gaggctgagg gaggtggatc acttgagtcc aggagtttga gaccagtctg ggcaacatgg    120

cgaaacttca tcactaccaa agaagaaaaa aattagccag gtgtggtggt gtatgcctgt    180

agtcccagat actctggtgg ctgaggtgag aggatagctt gagcccagga aattgaggct    240

gcagtgaact atgattgcac tactgtgctc cagcttgggc aacagagtga gatcttgtct    300
```

```
ccaaaagtcc ttgaaggatt ttaggaagtt gttaaaagtc ttgaaacgat gtttgggggc    360

atgttagggt tcttgaatgt ttaattcctc taataactgc ttattcaaga gaagcatttc    420

tgactgggtg cggggcagtg gcttcatgcc ccataatccc agtactttgg gaggctgaag    480

caggaacatt gcttgagccc aggacttcaa gaacagcctg ggtaacata                529


<210> SEQ ID NO 101
<211> LENGTH: 277
<212> TYPE: DNA
<213> ORGANISM: Homo sapien

<400> SEQUENCE: 101

tcgagcggcc gcccgggcag gtcgcaggaa gaggatggaa actgaggagt ccaggaagaa     60

gagggaacga gatcttgagc tggaaatggg agatgattat attttggatc ttcagaagta    120

ctgggattta atgaatttgt ctgaaaaaca tgataagata ccagaaatct gggaaggcca    180

taatatagct gattatattg atccagccat catgaagaaa ttggaagaat tagaaaaaga    240

agaagagctg agaacagacc tcggccgcga ccacgct                             277


<210> SEQ ID NO 102
<211> LENGTH: 490
<212> TYPE: DNA
<213> ORGANISM: Homo sapien

<400> SEQUENCE: 102

gcgtggtcgc ggccgaggtc tgacggcttt gctgtcccag agccgcctaa acgcaagaaa     60

agtcgatggg acagttagag gggatgtgct aaagcgtgaa atcagttgtc cttaattttt    120

agaaagattt tggtaactag gtgtctcagg gctgggttgg ggtccaaagt gtaaggaccc    180

cctgccctta gtggagagct ggagcttgga gacattaccc cttcatcaga aggaattttc    240

ggatgttttc ttgggaagct gttttggtcc ttggaagcag tgagagctgg gaagcttctt    300

ttggctctag gtgagttgtc atgtgggtaa gttgaggtta tcttgggata aagggtcttc    360

tagggcacaa aactcactct aggtttatat tgtatgtagc ttatattttt tactaaggtg    420

tcaccttata agcatctata aattgacttc tttttcttag ttgtatgacc tgccccgggc    480

ggccgctcga                                                           490


<210> SEQ ID NO 103
<211> LENGTH: 490
<212> TYPE: DNA
<213> ORGANISM: Homo sapien

<400> SEQUENCE: 103

gagcggccgc ccgggcaggt ccaaaccagc ttgctcataa gtcattaacc aaatccatta     60

taggtaattt gttcagttca atgtttacaa ttcttatgga aaaaattagc aacacacaca    120

tttaaaacgt gtgcatttac ctttgcgtga gtgcttaaaa tacatatttc tatttcaaga    180

tgacatttaa aaattattct aatatatcag cagcaaaaat ataatttgca attacaaaaa    240

actaaactag aatccttaag ttattctcat gtttacagtt gtgattcttt aataaatact    300

attatgcagc tctattgttt aagctttctg gatttggttt aaacacatgc atatatattg    360

tcaattgtgg gaagctttac aagttatatt ccatgcactt tttggacaga gttctaacag    420

agccagccag tccacaaaac aggcaagaca aaagttgaat taactggggc aaaataggac    480

tcttatgcaa                                                           490
```

<210> SEQ ID NO 104
<211> LENGTH: 489
<212> TYPE: DNA
<213> ORGANISM: Homo sapien

<400> SEQUENCE: 104
cgtggtcgcg gccgaggtcc aggctggtct cgaactcctg accttgtgat ctgcccgcct 60
cggcctccca aagtgttggg attacaggca tgagccactg cgcccgaccg agttgaacat 120
ttaatgtcag actaggccag agtttctcaa tctttttatt ctcacttccc aaaggagccg 180
ttggagattt tcccctcaat ctctctcctt catgaaattt cataccacaa atatagtatg 240
ttttatttat gtactgtgac cctttgaagg atcacaaacc aatataatag tttttctttt 300
taacccgtca aggaccaagt tttgcccct gttggaaatg cataaactgg actgatgaat 360
tggtatagat ggcttttatc atgaggatca gaaaaacttg aaattccttg gctacgacac 420
tccatattta tcaccgtata gggaggacct tggtatgggg aagtagaaac acttctacac 480
tttacagca 489

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105
gcgtggtcgc ggccgaggtc tgactggctt cagccccaga agttgagctg gcctttagac 60
aaaataattg cacctccctc tgctgcttat tcccttccgt ttttcatttg agtgtgaaca 120
gttagataaa atctgtggct gnctcttcca ccttgctcta gtttccattg ctgtgagcag 180
gccctcctat gccccgcatt tagctacaat gctgtggact cacttgattc tttttctccg 240
agctttgtct agaaatatgt gaaggtgagg ttaagtgctt ctctgtgtag atccacttag 300
ccctgtctgc tgtctcgatg ggcgttgctt cgtctctcct ctcttccatc ctttccattt 360
gcttctcacc accttctggc ttctttttctt aatgcaataa aggcagtttc taacaaagaa 420
agaatgtggg ctttggagtt agacagacct ggntttaaat tctgcttctg gctctccaa 479

<210> SEQ ID NO 106
<211> LENGTH: 511
<212> TYPE: DNA
<213> ORGANISM: Homo sapien

<400> SEQUENCE: 106
tcgcggccga ggtccaaaac gtggattcca atgacctgcc ttgagcccgc ggttgccagg 60
agttggacct gcagtagtat gggaagctca cggcctaaat accgactgcc ctctgacccc 120
accgtccagc gattctagaa catttctagt aggaaagaca tagcaaggga ttttcatgat 180
tgggaaatac tgggagacaa gctgaagatt tgttaagggc tatgcttctg tcatctttta 240
ggtatttaag gctactcctt tagctagcta ctttgagctg tttaaagtga ctatctccct 300
acacagagtt acacaatgag catctctgaa agagaatatt accctggatt tccaaagatg 360
tactctaaca ggatgaccag gcaaaaggtg acccggggga ggagtctgtt ataacactcg 420
gacccacatg ttctcaaggc acttcagaac tttgggaaat cattttgtac cggatcctca 480
gaaagcattt atggaaatac acatccttta g 511

<210> SEQ ID NO 107
<211> LENGTH: 451
<212> TYPE: DNA
<213> ORGANISM: Homo sapien

<400> SEQUENCE: 107

```
ggccgcccgg gcaggtccag aatatcaaat caaaaggtca caaatgttca cttcctcctc     60

caccctctta catattggat cttcaattgc aatagggagt gtaagatggg cattttagag    120

acgtagttgc atcagcagaa gcaaacccat cttatacaaa tgggttttgg ggataggaaa    180

aggctgctaa aaattcacaa gtcaccattc cccagaagca atgaatagcc gtagaagacc    240

aaggaagatc aacaagtttc caaagtgcta aagccagaga tttggccctt ccaaaatacc    300

accaggacgc ctggacccgt gggctctccg catgtcacca ctgactgcca ggatgctgct    360

gcacctccct tccttgagac acaacagaga gacagtgaag tcacccaaga ctgggatcat    420

cagaggctcc tcatgcttgc tacagagaag c                                   451
```

<210> SEQ ID NO 108
<211> LENGTH: 461
<212> TYPE: DNA
<213> ORGANISM: Homo sapien

<400> SEQUENCE: 108

```
ccgcccgggc aggtcctgaa aacattcaga ctaatcaaaa tggtactact gtaacttctt     60

ataatacata atataaaagt ttttgaaaga tatagacaca attaacccct aaacaacaca    120

ctatctgatt ctcaaaagca atggctattt aacaagatgt aaaaggacaa taacatatca    180

aagaactttc acacacctaa agatagcatt tagcagcaag ttagtcagac aaaacaaaca    240

caaatatttt cacatttcct atgtttgttt ttaactttac ttcataaagc cactgataat    300

tgaggtttct ttcaagtata agatttctaa aattaaaaac tgtttttgac atatttttat    360

aaagaaataa aaagcaaaac gcaatccaac tatttatatg agtccctctt ctccaacagc    420

tttagatggt tttctgagta ctttttttaca cagaatattt t                        461
```

<210> SEQ ID NO 109
<211> LENGTH: 441
<212> TYPE: DNA
<213> ORGANISM: Homo sapien

<400> SEQUENCE: 109

```
ggccgcccgg gcaggtctga ttataagaga aagaaatcca gtgacacgag ggcaggcagg     60

ccccgctctg ctctgatcga gaaaagcttc ctgatgtcag ggagatggaa ctgccaccat    120

cagaaccatg gcactttggg tgaaggtgtg tcagcgacca agggggcagg aaatgggcag    180

tgactaaggg ggcaggaaac aggcaggcac atggcaaggt tctcccagcc catcagccca    240

gtgatggcct cgattttgaa gctgcactac tgtctgaaaa gcacaattac tggtgactct    300

taacaaactt cagcatactg gggaaggaga ctgtcaagta actgaattgg aaagatgaaa    360

aagaaccatc tctaaaagtt gatgcttgtc agaagaataa cctcctttgt gcaagtcttg    420

caacatcttc attcaaccac a                                              441
```

<210> SEQ ID NO 110
<211> LENGTH: 451
<212> TYPE: DNA
<213> ORGANISM: Homo sapien
<220> FEATURE:

<221> NAME/KEY: misc_feature
<222> LOCATION: (1)...(451)
<223> OTHER INFORMATION: n = A,T,C or G

<400> SEQUENCE: 110

```
ggtcgcggcc gaggtctggg gaaggggtga gaatccctgg gccttgccca gtcctgagct     60
ctgggtgtct gcagggaagc acagtggtga gttagtgtta aagaaagcat ccagagaggt    120
aagaggggct tgggtagcac cctttgcctc tgtcacttcc gcaaaaactt cttgttgagg    180
aggaagatga gaaggttgac attgactttg gccttgttga agagtttcat gacagccaca    240
ccctcatact ggagctgcan gagatcctga tagtgaagct tgaaatcgct ccatgtccac    300
acccaggaac ttggcattta cttcaaactt tcctgcctca tctcccggcg tgatgtcaaa    360
natgacgttt cttgaagtga gaggcgggaa agatcttcaa tttccaccaa agacaccctt    420
tttccaggaa gcttgagcaa caagtgtaat g                                   451
```

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111

```
ggccgacgtt cgacctgact tctttngagc agntgncact acccgtcttg aggaatgccg     60
actgcagaca gtggcccang gcaaagagtg tgcgtcatcg atganattgg naagatggag    120
ctcttcagtc agnttttcat tcaagctgnt cgtcagacgc tgtctacccc agggactata    180
atcctnggca caatcccagt tcctanagga aagccactgn ctcttgtaga agaaatcana    240
cacanaaagg atgtgaacng tgtttaatgt caccaaggga aaacatgaaa ccaccttctg    300
ccagatatcg ggacgttgcg tgcagatcaa gcacgnaagt gaagacgcgt gcattccttg    360
ccttccgtga acgantgccc agntcaagaa gancctgatg gaaccct                  407
```

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

```
tcgcggccga ggtcggccga ggtctgacat ctgttgtctg tgataaccac ttctgtattg     60
cgtcttaacc acttctgtat tgtgtggttt taactgccta aggcggcaat gggcagtggg    120
cccctttccc ttaggatggg tatcaattca acaatattta taaggcattt actgtgtgct    180
aagcatttgg aagacccagg ctacaaaata agacatagtt cctgccctcc aggccagcag    240
agggaggcac aaatacccag gaatctctga tgggtgtgaa gtgcggtcgt gggccacaga    300
aaatgaccgt catggagacc ctgctaaagg tcggaccctg agcccaaagg ggtattcaga    360
agnggagatg attttggccc cactcataga tgggtggcaa a                        401
```

<210> SEQ ID NO 113
<211> LENGTH: 451
<212> TYPE: DNA
<213> ORGANISM: Homo sapien

<400> SEQUENCE: 113
gtcgcggccg aggtccatat taaaaagtcc atcataaaca aagactcctc ctcatggtat 60
gaatatgctc catatgccca taatggtgca taacggactt agaaattcca atgagtctta 120
gggttgaaat ttccaatgac ctgagcaagg cagctcccta tagcttctgg ataacatttt 180
acacccagag ttcaggctta aacagaccta tcaacacaat tattttcgga ttgtctgtct 240
agaaaacggc aatgctcaaa ggaatataaa taagggtggg gggacatatg cttccagcct 300
ggcctttctc catgtggtaa aaaacaatgg aatggctgtg ttaatttttt tttaatcttt 360
tctgaccttt actatgtttg gtaatggaaa taagtcaggg aaaacaaaat gaacaggtct 420
catcacttaa ttaatactgg gttttcttct t 451

<210> SEQ ID NO 114
<211> LENGTH: 441
<212> TYPE: DNA
<213> ORGANISM: Homo sapien

<400> SEQUENCE: 114
ggccgcccgg gcaggtccat cctgtcagag atgggagaag tcacagacgg aatgatggat 60
acaaagatgg ttcactttct tacacactat gctgacaaga ttgaatctgt tcatttttca 120
gaccagttct ctggtccaaa aattatgcaa gaggaaggtc agcctttaaa gctacctgac 180
actaagagga cactgttgtt tacatttaat gtgcctggct caggtaacac ttacccaaag 240
gatatggagg cactgctacc cctgatgaac atggtgattt attctattga taaagccaaa 300
aagttccgac tcaacagaga aggcaaacaa aaagcagata agaaccgtgc ccgagtagaa 360
gagaacttct tgaaacttga cacatgtgca aagacaggaa gcagcacagt ctcggcggga 420
ggaagaaaaa aagaacagag a 441

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115
gccgcccggg caggtccatt ggcggtgaca aaaggaaaag aagcaaagag actcagtcca 60
taatgctgat tagttagaag aaagggctag gattgagaaa gtaccaggaa cttttaatta 120
tttaaaagag aatgctgact gttaatgttt taaatcttac tgttcaaatg tactaatatg 180
aatttttacc ctttgtgcat gaatattcta aacaactaga agacctccac aatttagcag 240
ttatgaaagt taaacttttt attataaaaa ttctaaacct tactgctcct ttaccaggaa 300
catgacacac tatttancat cagttgcata cctcgccaat agtataattc aactgtcttg 360
cccgaacaat catctccatc tggaagacgt aagcctttag aaacacattt ttctattaat 420
ttctctagaa c 431

<210> SEQ ID NO 116
<211> LENGTH: 421
<212> TYPE: DNA
<213> ORGANISM: Homo sapien

<400> SEQUENCE: 116

-continued

```
gtcgcggccg aggtccagaa atgaagaaga agtttgcaga tgtatttgca aagaagacga     60

aggcagagtg gtgtcaaatc tttgacggca cagatgcctg tgtgactccg gttctgactt    120

ttgaggaggt tgttcatcat gatcacaaca aggaaccggg gctcgtttat caccagtgag    180

gagcaggacg tgagccccg ccctgcacct ctgctgttaa acaccccagc catcccttct    240

ttcaaaaggg atcctttcat aggagaacac actgaggaga tacttgaaga atttggattc    300

agcccgcgaa gagatttatc aagcttaact cagataaaat cattgaaagt aataaggtaa    360

aagctaagtc tctaacttcc aggcccacgg ctcaagtgaa tttcgaatac tgcatttaca    420

g                                                                    421
```

<210> SEQ ID NO 117
<211> LENGTH: 489
<212> TYPE: DNA
<213> ORGANISM: Homo sapien

<400> SEQUENCE: 117

```
agcgtggtcg cggccgaggt aaggctgcga ggttgtggtg tctgggaaac tccgaggaca     60

gagggctaaa tccatgaagt ttgtggatgg cctgatgatc cacagcggag accctgttaa    120

ctactacgtt gacactgctg tgcgccacgt gttgctcaga cagggtgtgc tgggcatcaa    180

ggtgaagatc atgctgccct gggacccaac tggtaagatt ggccctaaga agcccctgcc    240

tgaccacgtg agcattgtgg aacccaaaga tgagatactg cccaccaccc ccatctcaga    300

acagaagggt gggaagccag agccgcctgc catgccccag ccagtcccca cagcataaca    360

gggtctcctt ggcagacctg cccgggcggc cgctcgaaag cccgaattcc agcacactgg    420

cggccgttac tagtggatcc cagctcggta ccaagcttgg cgtaatcatg gtcatagctg    480

gtttcctgt                                                            489
```

<210> SEQ ID NO 118
<211> LENGTH: 489
<212> TYPE: DNA
<213> ORGANISM: Homo sapien

<400> SEQUENCE: 118

```
tcgagcggcc gcccgggcag gtattgaata cagcaaaatt ctatatacaa agtgacctgg     60

acctgctgct tcaaaacatg atcctttctt actaatatct tgatagtcgg tccatagagc    120

attagaaagc aattgactct taaataaaca gaaaagtgcc taatgcacat taaatgaatg    180

gcctaactac tggaacttta gtagttctat aaggtgatta acataggtag gatccagttc    240

ctatgacagg ctgctgaaga acagatatga gcatcaagag gccattttgt gcactgccac    300

cgtgatgcca tcgtgtttct ggatcataat gttcccatta tctgattcta gacacaccac    360

aggaatatca gtggggtcag aggttagctt agctgcttgc tgggctagaa cagatatcac    420

tccagcatgc tcatctgaca gggtcccgcg gcaacccaga ttaagtcctt gtgaatctgt    480

gcacaggga                                                            489
```

<210> SEQ ID NO 119
<211> LENGTH: 181
<212> TYPE: DNA
<213> ORGANISM: Homo sapien

<400> SEQUENCE: 119

```
taggttccag agacttttgg cccaggagga atatttactt ttagctctgg acatcattac     60

aaaaaggaat atttcccaaa cctcttcaga ccgagaatac atgggtaaaa ttattaaata    120
```

```
gttgtataat aaaaataatt ttttccttaa aaaaaaaaaa aacctcggcc gcgaccacgc    180

t                                                                    181


<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120

gcgtggtcgc ggccgaggtc catttaaaac aaagaaaaat actaaagcca ctagtaaaca     60

tctgatgtgc aaaatacaac atcctctagt tggctttatg ccattattac ataagctcca    120

aatagctcat cttaaattaa aaagaaaaag tggctgtccc atctctgctg cataaatcag    180

attttttttt aaaggtttag agtactttaa ggaagggaag ttcaaaactg ccagtgaaat    240

tcacagagaa tacaaattta gcaatttaat ttcccaaagc tctttgaaga agcaagagag    300

tctctcttct taatgcagtg ttctcccaag aggaactgta attttgcttg gtacttatgc    360

tgggagatat gcaaaatgtg tttttcaatg tttgctagaa tataatggtt cctcttcagt    420

gnctggttca tcctggaact catgggttaa gaaggacttc ttggagccga actgcccggg    480

cgggccntt                                                            489


<210> SEQ ID NO 121
<211> LENGTH: 531
<212> TYPE: DNA
<213> ORGANISM: Homo sapien

<400> SEQUENCE: 121

cgagcggccg cccgggcagg tggccagcgc tggtcccgca gacgccgaga tggaggaaat     60

atttgatgat gcgtcacctg gaaagcaaaa ggaaatccaa gaaccagatc ctacctatga    120

agaaaaaatg caaactgacc gggcaaatag attcgagtat ttattaaagc agacagaact    180

ttttgcacat ttcattcaac ctgctgctca gaagactcca acttcacctt tgaagatgaa    240

accagggcgc ccacgaataa aaaaagatga gaagcagaac ttactatccg ttggcgatta    300

ccgacaccgt agaacagagc aagaggagga tgaagagcta ttaacagaaa gctccaaagc    360

aaccaatgtt tgcactcgat ttgaagactc tccatcgtat gtaaaatggg gtaaactgag    420

agattatcag gtcccgagga ttaaactggc tcatttcttt gtatgagaat ggcatcaatg    480

gtatccttgc agatgaaatg ggcctaggaa agactcttca acaatttctc t             531


<210> SEQ ID NO 122
<211> LENGTH: 174
<212> TYPE: DNA
<213> ORGANISM: Homo sapien

<400> SEQUENCE: 122

tcgagcggcc gcccgggcag gtctgccaac agcagaggcg gggcctccgg catcttcaaa     60

gcacctctga gcaggctcca gccctctggc tgcgggaggg gtctggggtc tcctctgagc    120

tcggcagcaa agcagatgtt atttctctcc cgcgacctcg gccgcgacca cgct          174


<210> SEQ ID NO 123
<211> LENGTH: 531
<212> TYPE: DNA
```

<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123

```
agcgtggtcg cggccgaggt cctcaaccaa gagggttgat ggcctccagt caagaaactg     60

tggctcatgc cagcagagct ctctcctcgt ccagcaggcg ccatgcaagg gcaggctaaa    120

agacctccag tgcatcaaca tccatctagc anagagaaaa ggggcactga agcagctatg    180

tctgccaggg gctaggggct cccttgcaga cagcaatgct acaataaagg acacagaaat    240

gggggaggtg ggggaagccc tatttttata acaaagtcaa acagatctgt gccgttcatt    300

cccccagaca cacaagtaga aaaaaaccaa tgcttgtggt ttctgccaag atggaatatt    360

cctccttcct aanttccaca catggccgtt tgcaatgctc gacagcattg cactgggctg    420

cttgtctctg tggtctgggc accagtagct tgggccccat atacacttct cagttcccac    480

anggcttatg gccnangggc angctccaat tttcaagcac cacgaaggaa g             531
```

<210> SEQ ID NO 124
<211> LENGTH: 416
<212> TYPE: DNA
<213> ORGANISM: Homo sapien

<400> SEQUENCE: 124

```
tcgagcggcc gcccgggcag gtccatctat actttctaga gcagtaaatc tcataaattc     60

acttaccaag cccaggaata atgactttta aagccttgaa tatcaactaa gacaaattat    120

gccaattctg atttctcaca tatacttaga ttacacaaag ataaagcttt agatgtgatc    180

attgtttaat gtagacttat ctttaaagtt tttaattaaa aactacagaa gggagtaaac    240

agcaagccaa atgatttaac caaatgattt aagagtaaaa ctcactcaga aagcattata    300

cgtaactaaa tatacatgag catgattata tacatacatg aaactgcaat tttatggcat    360

tctaagtaac tcatttaagt acatttttgg catttaaaca aagatcaaat caagct        416
```

<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

```
agcgtggtcg cggccgaggt gctttttttt tttttttttt tttttttttt gctattctaa     60

aggggaaggc ccctttttat taaacttgta cattttactt tccttctttc anaatgctaa    120

taaaaaactt ttgtttatac ttaaaaaaac cataaatcan acaaacaaaa gaaacgattc    180

caacatcact tctgngatg                                                 199
```

<210> SEQ ID NO 126
<211> LENGTH: 490
<212> TYPE: DNA
<213> ORGANISM: Homo sapien

<400> SEQUENCE: 126

```
cgtggtcgcg gccgaggtcc agttgctcta agtggattgg atatggttgg agtggcacag     60

actggatctg ggaaaacatt gtcttatttg cttcctgcca ttgtccacat caatcatcag    120
```

ccattcctag agagaggcga tgggcctatt tgtttggtgc tggcaccaac tcgggaactg 180
gcccaacagg tgcagcaagt agctgctgaa tattgtagag catgtcgctt gaagtctact 240
tgtatctacg gtggtgctcc taagggacca caaatacgtg atttggagag aggtgtggaa 300
atctgtattg caacacctgg aagactgatt gactttttag agtgtggaaa aaccaatctg 360
agaagaacaa cctaccttgt ccttgatgaa gcagatagaa tgcttgatat gggctttgaa 420
ccccaaataa ggaagattgt ggatcaaata agacctgata ggcaaactct aatgtggagt 480
gcgacttggc 490

<210> SEQ ID NO 127
<211> LENGTH: 490
<212> TYPE: DNA
<213> ORGANISM: Homo sapien

<400> SEQUENCE: 127
cgtggtcgcg gccgaggtcg gccgaggtct ggagatctga gaacgggcag actgcctcct 60
caagtgggtc cctgacccct gacccccgag cagcctaact gggaggcacc ccccagcagg 120
ggcacactga cacctcacac ggcagggtat tccaacagac ctgaagctga gggtcctgtc 180
tgttagaagg aaaactaaca agcagaaagg acagccacat caaaaaccca tctgtacatc 240
accatcatca aagaccaaaa gtaaataaaa ccacaaagat gggaaaaaaa cagaacagaa 300
aaactggaaa ctctaaaaag cagagcacct ctcctcttcc aaaggaacgc agttcctcac 360
cagcaatgga acaaagctgg atggagaatg actttgacga gctgagaaaa gaacgcttca 420
gacgatcaaa ttactctgag ctacgggagg acattcaaac caaaggcaaa gaagttgaaa 480
actttgaaaa 490

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128
cgtggtcgcg gccgaggtgc tttttttttt tttttttttt tttttttttt tgctgattta 60
ttttttctnt ttattgttac atacaatgta taaacacata aaacanaaaa cagtagggat 120
cctctaggat ctctagggan acagtaaagt anaaagaggt ctcanaaaca tttttttaaa 180
gtacaagaca ttcagngctc ggcccaaagg cgtaaaaggt ttanagccag canatagctg 240
nactaaaggc tccgtctntn tccccanagc caggacaacc ccagggagct ntccattagc 300
agccagtcca cgcaggcagg atgctgcgga aaaagctcta tgctganaac attccccttg 360
atggaaagaa gggcaacaca aaaggggtaa ctaanagctc cttcctctcg tgagggcgac 420
aactgaggaa cagaaaagga gtgtcccatg tcacttttga ccccctccc 469

<210> SEQ ID NO 129
<211> LENGTH: 419
<212> TYPE: DNA
<213> ORGANISM: Homo sapien

<400> SEQUENCE: 129
gcgtggtcgc ggccgaggtc tgattttcat ttaaatattt cagagctata gcatttgcct 60

-continued

```
ccatgctcaa atccacacca ttggggctta agccgctcat gccaacatta gcaaatgaca    120

tgcagtttaa tccagagatc actgcttctg ggctgatgca tgccaacaca ctggcgtgat    180

ccacgttatg tgcatttttc ttcactttag tgggagaatc aatttttact ccaaggcttc    240

ttagttgctt aagagttgca ttaaggacac aatctttgtc caccagtctt gaatgatgtg    300

tttttttctt tgtatggtaa acgttttggg ttctggtgca ttcatgactg ataattactg    360

ctttggtaga cggctgctca agtttccttg gaggaactat ttaataggtg ggttacttg     419
```

<210> SEQ ID NO 130
<211> LENGTH: 354
<212> TYPE: DNA
<213> ORGANISM: Homo sapien

<400> SEQUENCE: 130

```
agcgtggtcg cggccgaggt ccatctgagg agataaccac atcactaaca aagtgggagt     60

gaccccgcag agcacgctgt ggaattccat agttggtctc atccctggtc agtttccaca    120

tgatgatggt cttatctcga gaggcggaga ggatcatgtc cgggaactgc ggggtagtag    180

cgatctgggt tacccagccg ttgtggccct tgagggtgcc acgaagggtc atctgctcag    240

tcatggcggc ggcgagagcg tgtgtcgctg cagcgacgag gatggcactg gatggcttag    300

agaaactagc accacaacct ctcctgccgc acctgcccgg gcggcccgct cgaa          354
```

<210> SEQ ID NO 131
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 131

```
cgagcggccg cccgggcagg tctggcagca gcttcctctg gaataattga cagctttgtg     60

ctgcctgact aaaatttgaa atgacaaccg ctgaatgtaa aatgatgtac ctacaatgag    120

agagatttag gaatactatc tgtcaatcca tagatgtaga aacaaaacaa actacagaat    180

gaaaacaaac ttattttaaa ccaaagaaac aaatgtatcc aaaatatagt ccatgatata    240

tttgattact agtataacca cagttgaaaa cttaaaaaaa aaaattgaca ttttttgtaa    300

tgggtactaa tggatttata aaaggtttct gtttccaaag atgttattgg ggtccacata    360

ttccttgaag acttcagcat cccaaagccc gacatcagag atactttcct ttagccattg    420

nttcccgtaa cttgcccact ccatggtgat gtgacaggct tcccttcatt agca          474
```

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132

```
ggccgaggtg ggaattcat gtggaggtca gagtggaagc aggtgtgaga gggtccagca     60

gaaggaaaca tggctgccaa agtgtttgag tccattggca agtttggcct ggccttagct    120

gttgcaggag gcgtggtgaa ctctgcctta tataatgtgg atgctgggca cagagctgtc    180

atctttgacc gattccgtgg agtgcaggac attgtggtag gggaagggac tcattttctc    240
```

-continued atcccgtggg tacagaaacc aattatcttt gactgccgtt ctcgaccacg taatgtgcca 300
gtcatcactg gtagcaaaga tttacagaat gtcaacatca cactgcgcat cctcttccgg 360
cctgtcgcca gccagcttcc tcgcatcttc accagcatcg ganaggacta tgatgaaccg 420
tgtgctgccg tccatcacaa ctgagatcct caagtcagtg gtggctcgct ttga 474

<210> SEQ ID NO 133
<211> LENGTH: 387
<212> TYPE: DNA
<213> ORGANISM: Homo sapien

<400> SEQUENCE: 133
tgctcgagcg gccgccagtg tgatggatat ctgcagaatt cggcttagcg tggtcgcggc 60
cgaggtctgc gggcccctta gcctgccctg cttccaagcg acggccatcc cagtagggga 120
ctttcccaca ctgtgccttt acgatcagcg tgacagagta gaagctggag tgcctcacca 180
cacggcccgg aaacagcggg aagtaactgg aaagagcttt aggacagctt agatgccgag 240
tgggcgaatg ccagaccaat gatacccaga gctacctgcc gccaacttgt tgagatgtgt 300
gtttgactgt gagagagtgt gtgtttgtgt gtgtgttttg ccatgaactg tggccccagt 360
gtatagtgtt tcagtggggg agaactg 387

<210> SEQ ID NO 134
<211> LENGTH: 401
<212> TYPE: DNA
<213> ORGANISM: Homo sapien

<400> SEQUENCE: 134
ggccgcccgg gcaggtctga tgaagaacac gggtgtgatc cttgccaatg acgccaatgc 60
tgagcggctc aagagtgttg tgggcaactt gcatcggctg ggagtcacca acaccattat 120
cagccactat gatgggcgcc agttccccaa ggtggtgggg ggctttgacc gagtactgct 180
ggatgctccc tgcagtggca ctggggtcat ctccaaggat ccagccgtga agactaacaa 240
ggatgagaag gacatcctgc gcttgtgctc acctccagaa ggaagttgct cctgagtgct 300
attgactctt gtcaatgcga ccttcaagac aggaggctac ctggtttact gcacctgttc 360
tatcacagtg agacctctgc catggcagaa caggggaagc t 401

<210> SEQ ID NO 135
<211> LENGTH: 451
<212> TYPE: DNA
<213> ORGANISM: Homo sapien

<400> SEQUENCE: 135
ggtcgcggcc gaggtctgtt cctgagaaca gcctgcattg gaatctacag agaggacaac 60
taatgtgagt gaggaagtga ctgtatgtgg actgtggaga aagtaagtca cgtgggccct 120
tgaggacctg gactgggtta ggaacagttg tactttcaga ggtgaggtgt cgagaaggga 180
aagtgaatgt ggtctggagt gtgtccttgg ccttggctcc acagggtgtg ctttcctctg 240
gggccgtcag ggagctcatc ccttgtgttc tgccagggtg gggtaccggg gtttgacact 300
gaggagggta acctgctggc tggagcggca gaacagtggc cttgatttgt cttttggaag 360
attttaaaaa ccaaaaagca taaacattct ggtccttcac aatgctttct ctgaagaaat 420
acttaacgga aggacttctc cattcaccat t 451

<210> SEQ ID NO 136

<211> LENGTH: 411
<212> TYPE: DNA
<213> ORGANISM: Homo sapien

<400> SEQUENCE: 136

```
ggccgcccgg gcaggtctga atcacgtaga atttgaagat caagatgatg aagccagagt     60

tcagtatgag ggttttcgac ctgggatgta tgtccgcgtt gagattgaaa atgttccctg    120

tgaatttgtg cagaactttg accccttta ccccattatc ctgggtggct tgggcaacag    180

tgagggaaat gttggacatg tgcaggtggg tccctttgct gcgtatttgg tgcctgaggc    240

tctgtggatt tcccctccat caatcatctt accctctcat ccccctcaga tgcgtctgaa    300

gaaacatctc tggtataaga aaatcctcaa gtcccaagat ccaatcatat tttctgtagg    360

gtggaggaag tttcagacca tcctgctcta ttatatccga agaccacaat g            411
```

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137

```
cggccgcccg ggcaggtcgg ttggtgcggc ctccattgtt cgtgttttaa ggcgccatga     60

ggggtgacag aggccgtggt cgtggtgggc gctttggttc cagaggaggc ccaggaggag    120

ggttcaggcc ctttgcacca catatcccat ttgacttcta tttgtgtgaa atggcctttc    180

cccggntcaa gccagcacct cgatgaaact t                                  211
```

<210> SEQ ID NO 138
<211> LENGTH: 471
<212> TYPE: DNA
<213> ORGANISM: Homo sapien

<400> SEQUENCE: 138

```
gccgcccggg caggtctggg ctggcgactg gcatccaggc cgtaactgca aatctatgct     60

aggcggggtc tcccttctgt gtgttcaagt gttctcgact tggattctta actattttaa    120

aaaatgcact gagtttgggt taaaaaccaa ccaccaaaat ggatttcaac acagctctaa    180

agccaagggc gtggccggct ctcccaacac agcgactcct ggaggccagg tgcccatggg    240

cctacatccc ctctcagcac tgaacagtga gttgattttt ctttttacaa taaaaaaagc    300

tgagtaatat tgcataggag taccaagaaa ctgcctcatt ggaaacaaaa actatttaca    360

ttaaataaaa agcctggccg caggctgcgt ctgccacatt tacagcacgg tgcgatgcac    420

acggtgacca aaccacggag gcaagcttct ggcactcaca ccacgacccg c            471
```

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139

```
gtcgcggccg aggtctgttc tttagctcag atttaaacct gctgtctctt ctttatttgc     60

agaatgaatt cccagttcct gagcagttca agaccctatg gaacgggcag aagttggtca    120
```

```
ccacagtgac agaaattgct ggataagcga agtgccactg ggttctttgc cctcccttca    180

caccatggga taaatctgta tcaagacggt tcttttctag atttcctcta cctttttgct    240

cttaaaactg cttctctgct ctgagaagca cagctacctg ccttcactga aatatacctc    300

aggctgaaat ttggggtggg atagcaggtc agttgatctt ctgcaggaag gtgcagcttt    360

tccatatcag ctcaaccacg ccgncagtcc attcttaagg aactgccgac taggactgat    420

gatgcatttt agcttttgag cttttggggg gtattctacc aaccaacagt ccatttggaa    480

a                                                                    481


<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140

gtcgcggccg aggtttccca tttaagaaaa atagatcttg agattctgat tcttttccaa     60

acagtcccct gctttcatgt acagcttttt ctttacctta cccaaaattc tggccttgaa    120

gcagttttcc tctatggctt tgcctttctg attttctcag aggctcgagt ctttaatata    180

accccaaatg aaagaaccaa ggggaggggt gggatggcac tttttttgt tggtcttgtt    240

ttgttttgtt ttttggttgg ttgggttccg ttatttttta agattagcca ttctctgctg    300

ctatttccct acataatgtc aatttttaac cataattttg acatgattga gatgtacttg    360

aggctttttt gntttaattg agaaaagact ttgcaatttt ttttttagga tgagcctctc    420

c                                                                    421


<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141

cgantngccc gcccgggcan gtctgtctaa ntttntcang gaccacgaac agaaactcgt     60

gcttcaccga anaacaatat cttaaacatc gaanaattta aatattatga aaaaaaacat    120

tgcaaaatat aaaataaata nnaaaaggaa aggaaacttt gaaccttatg taccgagcaa    180

atccaggtct agcaaacagt gctagtccta nattacttga tntacaacaa cacatgaata    240

ca                                                                   242


<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142

agcgtggtcg cggcncgang tccacagggc anatattctt ttagtgtctg gaattaaaat     60
```

```
gtttgaggtt tangtttgcc attgtctttc caaaaggcca aataattcan atgtaaccac    120

accaagtgca aacctgtgct ttctatttca cgtactgttg tccatacagt tctaaataca    180

tgtgcagggg attgtagcta atgcattaca cagtcgttca gtcttctctg cagacacact    240

aagtgatcat accaacgtgt tatacactca actagaanat aataagcttt aatctgaggg    300

caagtacagt cctgacaaaa gggcaagttt gcataataga tcttcgatca attctctctc    360

caaggggccc gcaactaggc tattattcat aaaacacaac tgaanagggg attggtttta    420

ctggtaaatc atgtgntgct aaatcatttt ctgaacagtg gggtctaaat cantcattga    480

tttagtggca gccacctgcc cggcggccgn tcgaagccca attctgcaga tatccatcac    540

actggcggcc g                                                         551
```

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143

```
cgagnggccc gcccgggcag gtatcttcac aaactcaaca aaggcactac atgagacttc     60

acattcccct agtccaatag ctgacaaatt tttgcaacgt tctgcaatgc gaattaactc    120

ttcatcaagt ggccgtaatc catttgcaca cactactagt tcaaccagtc tagggcatgt    180

cattcccaca cggccaagca catctttgct tactgatctc ccaaagtaca gatgggtggc    240

aggtatttca tagcgaaaga aggggtcaaa ttcttcttca tataanaaaa aatacatcac    300

taagttcact ttgggtgaat gtctgatgaa agcatcccag ctactcttct gaatagtatg    360

gaagtgtgtc tgtccaggat tctcactgac tacatcaatg cgcaaatgtt ctaatcgaac    420

atgtttttca gaagacaatg caagtaacaa ctcatcactc aataagtggt aagttcaggg    480

ctagttctct taagccgnga cactgatcag cacac                               515
```

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144

```
tgcattctct ntggatgcan acctgcccgt tggtagggac tntgctcaca cggaacatgg     60

acggttacac ctgtgccgtg ggtgacgtcc accagcttct ggatcatctc ggcgngggtg    120

ttgtggaagg gcagactatc cacctccatg cncacgatgc ccganacgcc actccggact    180

ntgtgctgca ccaanatgcc cagcattnta tcttcaagca nagcacttat cagggtcctt    240

ggcacac                                                              247
```

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145
cgtgggtcgc ggcccgangt ctgctgtaac aaaacaccat agtctgggca gctcatagac 60
aatggaattt tatttctcac gcttctggag gctggattcc aagatcaagg ttccaggaga 120
ctcagtgtct ggcaaggtct cggtttctgc ctcanagatg gtgccatctg gctgtgtcct 180
cacaagtagg aaggtgcaag aagctcccct caggctctgt ctgtaagaca ctgatcccat 240
tcatganggg gaaacgtaat gacctaatca gcccccagag accccacttc taacaccatc 300
accttgggg 309

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146
agcgtgggtc gcggcncgac gtcctgtcca tatttcacag cccgagaact aatacaagat 60
gctgacatca tattttgtcc ctacaactat cttctanatg cacaaataag ggaaagtatg 120
gatttaaatc tgaaagaaca ggttgtcatt ttanatgaag ctcataacat cgaggactgt 180
gctcgggaat cagcaagtta cagtgtaaca gaagttcagc ttcggtttgc tcgggatgaa 240
ctanatagta tggtcaacaa taatataagg aaganagatc atgaacccct acgagctgtg 300
tgctgtagcc tcattaattg gntagaagca aacgctgaat atcttgnana angagantat 360
gaatcagctt gtaaaatatg gagtggaaat gaaatgctct taactttaca caaaatgggt 420
atcaccactg ctacttttcc cattttgcng gtaagatatn ttttctacct gngaaacgta 480
tttaag 486

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147
gccgcccggg cangttcgac attacntnga gttccatgat gtacaattct ttcacgaaaa 60
acaatgaatg caagaatttg aggatctcct tactcctccc ttttacagat ggtctctcaa 120
tcccttcttc ttcctcttca tcttcatctt cttctgaacg cgctgccggg taccacggct 180
ttctttgtct ttatcgtgag atgaaggtga tgcttctgtt tcttctacca taactgaaga 240
aatttcgctg caagtctctt gactggctgt ttctccgact tcgcctttnt gtcaaacgng 300
agtcttttta cctcatgccc ctcagcttca cagcatcttc atctggatgt tnatttctca 360
aagggctcac tgaggaaact tctgattcan atgtcgaana gcactgtgaa gttttctctt 420
cattttgctg 430

<210> SEQ ID NO 148
<211> LENGTH: 483
<212> TYPE: DNA
<213> ORGANISM: Homo sapien
<220> FEATURE:

-continued

```
<221> NAME/KEY: misc_feature
<222> LOCATION: (1)...(483)
<223> OTHER INFORMATION: n = A,T,C or G

<400> SEQUENCE: 148

cccgggcagg tctgtgttgn tttncaaccg gtgtcctccc cagcgtccag aananggaaa     60

tgtggagcgg gtgatgatga cccctcgctg tcctgtcacc tcctgcacag cttcgtatgt    120

gggtctggtc tgggaccacc cgtacaggtt gtgcacgttg tagtgctcca cgggggagct    180

gtccggcagg atctgctgac tctccatgca cagagtcttg ctgctcaggc ccttgtccct    240

agattccaaa tatggcatat agggtggggt tatttagcat ttcattgctg cagcccctga    300

cagatccatc cacaaaattt gatggctcat tcatatcaat ccacaatcca tcaaacttca    360

agctcttctc tggntctcga nggtttgcat agaactcttc tatctctttc ttccaccacg    420

canacctcgg ncgcgaccac gctaagccga attctgcana tatccatcac actggcggcc    480

gct                                                                  483


<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149

ctttcacgaa nacaatgaat gcaagaattt gaggatctcc ttactcctcc cttttacaga     60

tggtctctca atcccttctt cttcctcttc atcttcatct tcttctgaac gcgctgccgg    120

gtaccacggc tttctttgtc tttatcgtga gatgaaggtg atgcttctgt ttcttctacc    180

ataactgaag aaatttcgct gcaagtctct tgactggctg tttctccgac ttcgcctttt    240

tgcaaacgtg agtcttttta cctcatgccc ctcagcttcc acagcatctt catctggatg    300

ttcatttctc aaagggctca ctgaggaaac ttctgactca catgtcgaag aagcactgng    360

agtttctctt catttgctgc aaanttgctc tttgctggct gngctctcag accacccatt    420

tggctgcatg gggctgac                                                  439


<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

ggcncgcccg ggcangtcca ctccactttt gagctctgag ggaatacctt caggagggac     60

agggtcaggg agtcctggca gctccgcagc agagattcac attcattcag agacttgttg    120

tccagtgcaa tgccattgat cgcaacgatc ctgtctccca cagcaaggga cccttcttta    180

gcggcagggc ttccaggcag cacagcggca gcatacactc cattctccag actgatgcca    240

ctgtctttct gtccactgan gttgatgtgc agcggcgtga ccaccttccc acccagggac    300

ttcctccgcc gcacgaccat gttgatgggc cccctnccca ttgaggagcg ccttgatggc    360

ctgcttcttg nccttggtga tgaagtccac atcggtgatt ctcacagcca gtcattgacc    420

cttaagcggn catcagcaat gcttcctttg gccactttag ngacaaatat gccacagtcc    480
```

```
ccgggaaaca agggtcattc acaccttctg gcatatcaaa cacctcggcc gggancacta    540

agccgaattc tgcagatatc catcacactg gngggccg                            578


<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151

cgagcggccc gcccgggcag gtctgggaga tcagcgactg ctgccacgtg cccagaaatg     60

gctcgtcctt tcactacagc ggaatgcaat gagggtgggt gagaagatga tgggtcggtt    120

atttcattcc ttttcttttt acaacttcac tttcagagac ttcagcgttc catgtctgct    180

gtgctgtgga acccagagtg ctcttgcctg gatggctgag aatcccttgg accctggaag    240

cacctactcc atgatggccc ggtatagtgc aggctcaata taatcttccc ggtatcttga    300

gttgataact cgttgccgtt tcttttcttg cttaacctct ttctctgtga aaatctcatt    360

gaagcgcatg tctgaagcta ctgacagtct anatttgact ctcttgggaa gctcttcatc    420

cagtgtgtat acatcatctc tcttaaccac aagttggagc catncttaaa cttcacctgg    480

tacatttgga tagggtggga ggc                                            503


<210> SEQ ID NO 152
<211> LENGTH: 553
<212> TYPE: DNA
<213> ORGANISM: Homo sapien
<220> FEATURE:
<221> NAME/KEY: misc_feature
<222> LOCATION: (1)...(553)
<223> OTHER INFORMATION: n = A,T,C or G

<400> SEQUENCE: 152

agcgtggtcg cggcccgagg tccactgagc tccgccttcc ccgggctccc tgaggaagca     60

gagtcctgac ttccaggaag gacaggacac agaggcaaga actcagcctg tgaggctctg    120

ggtggctcct gaggccagag gacgccttcc gcgatccatg gctcagcatc gtccttctgg    180

cttcccagcc ccgggccgaa cgttcgggtt aataagcaga gcagttattc ggctcctggc    240

aggagctccc ccgttagttt ccacgttgtg agcacattca tacttaagac tgnttctctt    300

tgtgttttaa gcgtctgtct ctgtagtaaa ctgaaatgtt aacagaaatg cagacctgcc    360

cgggcggccg ctcgaaagcc gaattctgca gatatccatc acactggcgg ccgctcgagc    420

atgcatctag anggcccaat tcgccctata gtgagtcgna ttacaattca ctgggccgcg    480

ntttacaacg tcgtgactgg gaaaaccctg cggtacccac ttaatcgcct tgcagnacat    540

ccccctttcg cca                                                       553


<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153
```

-continued

```
tcgagcggct cgcccgggca ggtccaccta gcatggctcc tctaaacacg caactcagcg      60

aggggacccc cttcacctct ggcaagagag ctgggtagat cagaaacttg gtgacacctg     120

gctagcacag agcaggctca cttgtcttgg tcccactacc cagattcctg cagacattgc     180

aaaccaaatg aaggttgntg aatgacccct gtccccagcc acttgttttg gtatcatctg     240

ctctgcagtg gaatgcctgt gtgtttgagt tcactctgca tctgtatatt tgagtataga     300

aaccgantca agtgatctgt gcatncagac acactggggc acctgancac agaacaaatc     360

accttaacga tctggaatga aactgnganc antgcccgcc tgggtgggtc tgganaaact     420

gccgncttct tgttggacct tggccgcacc acct                                 454
```

```
<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154

agcgtggtcg cggcccgang gcggcctcct gantganggg aagggacgtg gggcggcca       60

cggcaggatt aacctccatt tcagctaatc atgggagaga ttaaagtctc tcctgattat     120

aactggttta naggtacagt tccccttaaa aagattattg tggatgatga tgacagtaag     180

atatggtcgc tctatgacgc gggcccccga agtatcaggt gtcctctcat attcctgccc     240

cctgtcagtg gaactgcaga tgtctttttc cggcagattt tggctctgac tggatggggt     300

taccgggtta tcgctttgca gtatccagtt tattgggacc atctcgagtt cttgtgatgg     360

attcacaaaa cttttanacc atttacaatt ggataaagtt catctttttg gcgcttcttt     420

gggangcttt ttggcccana aatttgctga atacactcac aaatctccta gaagccattc     480

cctaatcctc tgcaattcct tcagngacac ctctatcttc aaccaacttg gactggaaac     540

agctttggct gatgcctgca tttatgctca aaaaatagtt cttggaaatt ttcatc         596
```

```
<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155

ctcganttgg cncgcccggg cangtctgcc tggtttttga ccgngcgagc tatttagnct      60

ctggctctgt ttccggagct caaggnaaaa atcttgaana actcgagcag cttctgtgga     120

tagccttggg tacacatact gccgagcata gccaatgtac tttctcaata gctggtgggg     180

aatgggatct attgtttctc caggaaccac ctttagtctt tctgataatg gcttctcaga     240

aactacttca agtacggaag tatttgaatc ttgactatnc atacgagcta ctgtggcact     300

gctaatgggn tctctgctnt ccagctctta ttgcaatcac atg                        343
```

```
<210> SEQ ID NO 156
<211> LENGTH: 556
<212> TYPE: DNA
<213> ORGANISM: Homo sapien
<220> FEATURE:
<221> NAME/KEY: misc_feature
```

<222> LOCATION: (1)...(556)
<223> OTHER INFORMATION: n = A,T,C or G

<400> SEQUENCE: 156
tcgagcggcc cgcccgggca ggtctggcac cacncagatc gattaactgg ctcatctgat 60
ctcgtggccc ccaccctgga actgacttag cacaaaagga cacctcaatt ccttatgatt 120
tcatctccga cccaaccaat caacaccctt gactcactgg ccttcccct cccaccaaat 180 tatccttaaa aactctgatc cccgaatgct cagggagatc gatttgagta ctaataagac 240
tccagtctcc tgcacaagca gctctgtgta ctcttcctct attgcaattc ctgtcttgat 300
aaatcggctc tgtgtaggcg gcggaagaag tgaacctgtt gggcggttac cacctctgtc 360
gtgtgtgaca gttgntttga atctctaatt gctcagtaca gatccacatg caggttaagt 420
aagaagcttt tgaagaaaat ggaaagtctt aagtgatggc ttccaagaaa tcaaacctac 480
attaattagg gaacaacgga ctttacgtat cacaaatgaa gagactgacn aagtaaatca 540
acttggcctt ttctta 556

<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157
ggtccacaaa aatatatnaa ataagctgga tatataaaan caaacactta acatngncan 60
cattccttca gttattcaaa ctcactgata nctaacnggg agnagttggn attctggaag 120
acttcctaag ctaaaagtat atttacatat ttacaacaca ngtaaatata acngaagaac 180
tacttcaaat aangnngaaa ttccagaatt ctanagattt atagctatag ntnacaanta 240
tcaccaattg gtttgcaatc aanngnccag cactacttat gannaangtt taactannaa 300
accaaaaggg gagaaaacct ggnagggaaa nat 333

<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158
tcgagcggcc gcccgggcag gtctggtaca tttgtgcgag gtccggcact ctgttctcat 60
ccagtaagtg gtcgagccct ttctgcagaa ttgctgttaa atgttctcct aatagctgtt 120
tctccacaca agcaatcagt ggtttctgtg tgctgtggtc caagtaagtg attactctgt 180
ctccctcttc ttctaagcgt ttacttacat ggttaagata ttctggaacc tctctttcct 240
gcattaacct ttggccttcg gcagcatata agcaattagt ctcttccaaa aatttcagtt 300
caaatgaatc tttatacacc tgcaggtcag acagcatgcc caggnaggct ccgcaacagg 360
ctccggtcca cggcctcgcc gctcctctcg cgctcgatca gcagtaggat tccatcaatg 420
gttttactct gaaccatttt atcactaata atatgggttc taaacagttc taatcccata 480
tcccagatgg agggcagcgt ggagttctgc agcacatagg tgcggtccaa gaacaggaag 540

-continued

```
atgcttctga tcatgaatca tttgnctggc aatggtcctg ccagcacgtg gtaatctttc    600

ttttaaaaat aaacccttat ctaaacgtc                                      629


<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159

tcgagcggcc gcccgggcag gttctagagg ganaatctgg ctgatttggg aataaaatat     60

aatcgaatat tcaacaccat gaagataaat cttattttgg aaatctactg accttaatac    120

cccaagcttg ccctgaatac tttgattgga attggaatat atcaaaaaag gttagtattt    180

ttgttgtagt taggatacta aaaggatatt agttacccaa gagatccaat ttgtttttct    240

gatgaatagt gttcagtaaa atgaagcagt cttaagagtg actaataatt tcaaagtgat    300

ttttcgtcta ttcttaatat tttttaatta tttattttta agagttttat accttgagca    360

gatacaatga tccgctttag tgagaggaca atttctgatt gattgttttc tcttcaggcc    420

atctcacctc ttcattctct tgttacattt gaagcagttg atataatggg tttatacttt    480

aaaagataga catggtgcca tgaagtttgg ggaagttggg tgaattatcc cattctagtt    540

acagangagc tttccttaaa tgccctttac ttctangttt ggtcaagaag tcattttctg    600

agtaaaagtt attttcatat atgttgggg                                      629


<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160

tcgagcggcg cgcccgggca ggtctgctgg gattaatgcc aagttnttca gccataaggt     60

agcgaaatct agcagaatcc agattacatc cacttccaat cacgcggtgt ttgggtaatc    120

cacttagttt ccagataaca tacgtaagaa tgtccactgg gttggaaacc acaattatga    180

tgcaatcagg actgtacttg acgatctgag gaataatgaa tttgaagaca ttaacatttc    240

tctgcaccag attgagccga ctctcccctt cttgctgacg gactcctgca gttaccacta    300

caatcttana attgggcggg tcacagaata atctttatct gccacaattt taggtgctga    360

agaaataagc tcccatgctg cagatccatc atttctnctt taagcttatc ttccaaaaca    420

tccacaagan caangttcat cagccagaga ctttcccaga atgctgatag nacacgccat    480

accaacttgt ccaacancca ctacagcgat cttattggt                           519


<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161
```

```
cgagnggccc gcccgggcag gtccagtaag cntttnacga tgatgggaaa ggttatgcaa     60

ggtcccagcg gtacaacgag ctgtttctac atcatttgta ttctgcatgg tacgtacaat    120

agcagacacc atctgaggag aacgcatgat agcgtgtctg gaagcttcct ttttagaaag    180

ctgatggacc ataactgcag ccttattaac caccacctgg tcctcgtcat ttagcagttt    240

tgtcagttca gggattgcac gtgtggcang ttctgcatca tcttgatagt taatcaagtt    300

tacaactggc atgtttcagc atctgcgatg ggctcagcaa acgctggaca ttantgggat    360

gagcagcatc aaactgtgta natgggatct gcatgccctc atctaatgtc tcagggaaca    420

tagcagctcg taccctctga gctcga                                         446
```

```
<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162

agcgtngtcg cggcccgang tcctgggaag cctttnttgc tgagcctcac agcctctgtc     60

aggcggctgc ggatccagcg gtccaccagg ctctcatggc ctccgggctg ggaggngggt    120

gagggcacaa aacccttccc aaggccacga anggcaaact tggtggcatt ccanagcttg    180

ttgcanaagt ggcggnaacc cagtatccgg ttcacatcca ggntgatgtc acgaccctgg    240

gacatgtang cacataatcc aaaccggaga gcatcggtgc cacattcacg aatccccgct    300

gggaagtcag ctttctgccc ttctttggcc ttctccacct cgctgggatc cagg          354
```

```
<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163

tttttcncca agtcctcttg ccgngggatc tngactgcaa tttaagacac ttctaattag     60

ttatacccag gccctgcaaa attgctgggt ttatataata tattcttgct gcacgaagat    120

ttattattct gttggatgat tctattttaa ttntatttat tctggccaaa aaagaacctt    180

ctccgctcgt caagagangc caatntgtct tgaaggacaa gagaaagatg ctaacacaca    240

ctttcttctt cttgagga                                                  258
```

```
<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164

ggaacatatt acttttaaat tacttgggtc aatgaaacat ttaataaaaa catttgcttc     60

tctatataat acgtatgtat aaaataagcc ttttcanaaa ctctggttct cataatcctc    120
```

tataaatcan atgatctgac ttctaagagg aacaaattac agnaaggggt atacattnat 180
gaatactggt agtactagag ganngacgct aaaccactct actaccactt gcggaactct 240
cacagggtaa atgacaaagc caatgactga ctctaaaaac aa 282

<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165
gcccgggcan gtcctgtaat cccagctact cangangctg agtcatgana atcgcctgaa 60
tccgggaggt agaggccgca gcgagcaaag attaagccac tgcactccag tctgggtgac 120
agagtgagaa tctgtctgtt gctcctctgg cattggtctg aaatgggttt gtagaacatg 180
ccacagaagg accagcanca gcaacaaatg gatttgtgga angcgtagct ccaaatggag 240
cangcacact tgatgaagca cgctgtgtct gtgcagangc aaccactggc actgttccaa 300
aaacattgct gctagcatta cttgtggaag tatacgcatt actggaggtg gctgcanaac 360
tgaaaacgct gtctagttct gccanagctg catacttgnc tgaanatgca cttgactgac 420
tgggaactga accacanaac caacaggacc tttacctgtg ga 462

<210> SEQ ID NO 166
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 166
cgtgggtcgc ggcncgangt ctgaaaccaa tccagaacta aacatcagca cacaaaaaat 60
accaggatag atggaatcaa aagactctga agccaaaagg aggctaggga gagcaactga 120
acttagcaag ctgaggactt cagtgtccat catccgatcc tgccctgtaa caacaggtct 180
atatgataga gatattccat ctgagctgga ggccattatc cttagcaaac taacacagaa 240
cagaaaacca aatacatgtt ctcatttaga agtaggagct aaatgatgag aactcaagga 300
cacaaagaaa ggaacaacag acactggggc ctacttgagg gtggagggtg ggaggaggga 360
gaaga 365

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167
agcgtggtcg cggcgcgang tccagcccta gcttgcctgt gactccgcct tcactgggtg 60
ctctctctaa aagttgctga ctctttactg tatctcccaa ttcccactcc attggttcca 120
taaggggagg ggtgtctcac tcaacatggt gttcctggta ccaagaactg gctgacgaag 180
ctgggtgccg tggctcatgc ctgtaatccc agcactttg ggaggccaag aagggcggat 240
cacctgaggt ctggagttca agatcagcct gaccaacatg atgaaaccaa gtctccacta 300
aaaatataaa acaattagcc aggcatggtg gtgggtgcct gnaatcccag ctactgggga 360 ngct 364

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168
cccgggcagg tcaaaaccca aaacctttca ttttagccca aaccagctca tgattaggta 60
tacaaggata acagaaccag ttgtcaggac gagcatttga caagtaaaag caattcttgc 120
aaagctgcag ttcatccagc tcatggcatg tgtctttata tagcatcctc gcaatgtcag 180
cttgctcact gtctgctcca tagaaaatca cggtattgtg gagaagcaat tgggcatcag 240
ctttgaactc ttcataactt cggtatttcc cttcattcac tttctcttga atggtgggaa 300
cgtccacaga cctcggccgc gaccacgcta agcccgaatt ctgcagatat ccatcacact 360
ggcggccgtt cgagcatggc atctagaagg cccaattcgc ctatagngag tcgnattacc 420
aattcactgg ccgtcgnttt acaacgc 447

<210> SEQ ID NO 169
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 169
cgantngcgc gcccgggcag gtctgagcag cctttctgnn tgctggacta ttgggattgg 60
gttcatccaa cagagactgt atggatgtta gaatggaaga cacatcatag gttggactcc 120
aacggttctg aagtatgtcc agacatatac taccatctgc atagactaag aacaaagaag 180
taggtacatt aaacgtaaca agaccactaa ggttttaaca ttatagacaa aacanaaata 240
gtcaaganta ctttgctttt gaagtttaaa gattcctatg ttgcttccca gttaactgcc 300
taaaaagata agncataacc accactagtg aaataatcan gatgatcaga gaatgtcana 360
tgtgatcagt ataaaactgg angatattna gtgtcatcct ttggaaaagg ctgccctatn 420
atccaggaaa tcanaaacat tnttgaacag ggnccctagc tatccacaga catgtgggaa 480
attcattccc caaatngtag gctggatccc ctatctgaaa taac 524

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgancggcn cgcccgggca ggtgacaaac ctgttattga agatgttggt tctgatgagg 60

-continued aanaanatca gaagggatgg tgacaagaan aanaanaaga agattaagga aaagtacatc 120
gatcaagaag agctcaacaa aacaaagccc atctggacca gaaatcccga cgatattact 180
aatgangagt acggagaatt ctataanagc ttgaccaatg actgggaaga tcacttggca 240
gtgaagcatt tttcagttga nggacagttg gaattcagag cccttctatn tgtcccacga 300
cgtgctcctt ttgatctgtt tganancaga aa 332

<210> SEQ ID NO 171
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 171
cgagnggcnc gcccgggcag gtctgttgat agcgacttaa cagaaaagtc tagacaaaca 60
taagcataaa aaattacagt ctttctaccc ttgggaatgg ggagaaaaag gaatctctac 120
cccaagacca gaaataataa gtcctgtttc tggtcctgaa catccagaat tatggaggct 180
ttggcctgac accacattan aatttggtct ggaaatcaaa ctttaganac angagatcgt 240
aagccatttt atactatcga cctaaattcc agtctaacgg ttcctttaca aagttgcgga 300
aagccctctt atatgctagc tgtaggaaat atag 334

<210> SEQ ID NO 172
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172
agcgtggtcg cggcccgang tctgcctata aaactagact tctgacgctg ggctccagct 60
tcattctcac aggtcatcat cctcatccgg gagagcagtt gtctgagcaa cctctaagtc 120
gtgctcatac tgtgctgcca aagctgggtc catgacaact tctggtgggg cgagagcagg 180
catggcaaca aattccaagt tagggtctcc aatgagcttc ctagcaagcc agaggaaggg 240
cttttcaaag ttgtagttac ttttggcaga aatgtcgtag tactgaagat tcttctttcg 300
gtggaagaca atggatttcg ccttcacttt ctgccttaat atccactttg gtgccacaca 360
acacaatggg gatgntttca cacacttngn accanatctc tatgccagnt aggccatttt 420
ggaagnactt cganggtac 439

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173
cgatnggccg cccgggcagg tcctgtaaaa naggaaattc agacatcgta cgactcgtaa 60
ttgaatgtgg agctgactgc aatattttgt caaagcacca gaatagtgcc ctgcactttg 120
cgaagcagtc taacaatgtg cttgtgtacg acttgctgaa gaaccattta gagacacttt 180

```
caagagtagc agaagagaca ataaaggatt actttgaagc tcgccttgct ctgctagaac    240

cagtttttcc aatcgcatgt catcgactct gtgagggtcc agatttttca acagatttca    300

attaccaacc cccacagaac ataccagaag gctctggcat cctgctgttt atcttccatg    360

caaacttttt gggtaaagaa gttattgctc ggctctgtgg accgtgtagt gtacaagctg    420

tagttctgaa tgataaattt cagcttcctg tttttctggg tctcgctctg ttgtccaggc    480

tggagtgcag tggcgcggat tacagctcac tggagtcttg acttcccagg cacaagcaat    540

cctcccacct cagcctccta actacctggg actaaaaatg caccgccacc acattccgg     599


<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174

tcgatttggc cgcccgggca ggtccatgcn gnttntgccc attcccatgg ngcccgacaa     60

ncccatcccc gaggccgaca tccccatgtt catgttcatg cccaccatgc cctggctcat    120

ccctgcgctg ttccccagag gggccattcc catggtgccc gtcattacac cgggcatgtt    180

cataggcatg ggtcccccca ggagagggtt agnttgaggc cggacaggaa gcatgtttga    240

tggagaactg aggttcacag nctccaaaac tttgagtcat cacattcata ggctgctgca    300

tattctgtct gctgaatcca ttgtatncag tgatggcctg ctggggnttt ggaaggctng    360

cataccaggt agtaagntcg tctaggctga tgtttacacc tggggtcaga ccaagtanga    420

gggcaaggtt ttgctgactg attttctgga cccatatc                            458


<210> SEQ ID NO 175
<211> LENGTH: 1206
<212> TYPE: DNA
<213> ORGANISM: Homo sapien

<400> SEQUENCE: 175

ggcacgagga agttttgtgt actgaaaaag aaactgtcag aagcaaaaga aataaaatca     60

cagttagaga accaaaaagt taaatgggaa caagagctct gcagtgtgag gtttctcaca    120

ctcatgaaaa tgaaaattat ctcttacatg aaaattgcat gttgaaaaag gaaattgcca    180

tgctaaaact ggaaatagcc acactgaaac accaatacca ggaaaaggaa aataaatact    240

ttgaggacat taagatttta aaagaaaaga atgctgaact tcagatgacc ctaaaactga    300

aagaggaatc attaactaaa agggcatctc aatatagtgg gcagcttaaa gttctgatag    360

ctgagaacac aatgctcact tctaaattga aggaaaaaca agacaaagaa atactagagg    420

cagaaattga atcacaccat cctagactgg cttctgctgt acaagaccat gatcaaattg    480

tgacatcaag aaaaagtcaa gaacctgctt tccacattgc aggagatgct tgtttgcaaa    540

gaaaaatgaa tgttgatgtg agtagtacga tatataacaa tgaggtgctc catcaaccac    600

tttctgaagc tcaaaggaaa tccaaaagcc taaaaattaa tctcaattat gccggagatg    660

ctctaagaga aaatacattg gtttcagaac atgcacaaag agaccaacgt gaaacacagt    720

gtcaaatgaa ggaagctgaa cacatgtatc aaaacgaaca agataatgtg aacaaacaca    780

ctgaacagca ggagtctcta gatcagaaat tatttcaact acaaagcaaa aatatgtggc    840
```

-continued

```
ttcaacagca attagttcat gcacataaga aagctgacaa caaaagcaag ataacaattg    900

atattcattt tcttgagagg aaaatgcaac atcatctcct aaaagagaaa aatgaggaga    960

tatttaatta caataaccat ttaaaaaacc gtatatatca atatgaaaaa gagaaagcag   1020

aaacagaagt tatataatag tataacactg ccaaggagcg gattatctca tcttcatcct   1080

gtaattccag tgtttgtcac gtggttgttg aataaatgaa taaagaatga gaaaaccaga   1140

agctctgata cataatcata atgataatta tttcaatgca caactacggg tggtgctgct   1200

cgtgcc                                                              1206


<210> SEQ ID NO 176
<211> LENGTH: 317
<212> TYPE: PRT
<213> ORGANISM: Homo sapien

<400> SEQUENCE: 176

Met Gly Thr Arg Ala Leu Gln Cys Glu Val Ser His Thr His Glu Asn
 1               5                  10                  15

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300
```

-continued

```
Tyr Gln Tyr Glu Lys Glu Lys Ala Glu Thr Glu Val Ile
305                 310                 315


<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177

ccaatcatct ccacaggagc                                                 20


<210> SEQ ID NO 178
<211> LENGTH: 1665
<212> TYPE: DNA
<213> ORGANISM: Homo sapien

<400> SEQUENCE: 178

gcaaactttc aagcagagcc tcccgagaag ccatctgcct tcgagcctgc cattgaaatg     60

caaaagtctg ttccaaataa agccttggaa ttgaagaatg aacaaacatt gagagcagat    120

cagatgttcc cttcagaatc aaaacaaaag aaggttgaag aaaattcttg ggattctgag    180

agtctccgtg agactgtttc acagaaggat gtgtgtgtac ccaaggctac acatcaaaaa    240

gaaatggata aaataagtgg aaaattagaa gattcaacta gcctatcaaa aatcttggat    300

acagttcatt cttgtgaaag agcaagggaa cttcaaaaag atcactgtga acaacgtaca    360

ggaaaaatgg aacaaatgaa aaagaagttt tgtgtactga aaaagaaact gtcagaagca    420

aaagaaataa aatcacagtt agagaaccaa aaagttaaat gggaacaaga gctctgcagt    480

gtgaggtttc tcacactcat gaaaatgaaa attatctctt acatgaaaat tgcatgttga    540

aaaaggaaat tgccatgcta aaactggaaa tagccacact gaaacaccaa taccaggaaa    600

aggaaaataa atactttgag gacattaaga ttttaaaaga aaagaatgct gaacttcaga    660

tgaccctaaa actgaaagag gaatcattaa ctaaaagggc atctcaatat agtgggcagc    720

ttaaagttct gatagctgag aacacaatgc tcacttctaa attgaaggaa aaacaagaca    780

aagaaatact agaggcagaa attgaatcac accatcctag actggcttct gctgtacaag    840

accatgatca aattgtgaca tcaagaaaaa gtcaagaacc tgctttccac attgcaggag    900

atgcttgttt gcaaagaaaa atgaatgttg atgtgagtag tacgatatat aacaatgagg    960

tgctccatca accactttct gaagctcaaa ggaaatccaa aagcctaaaa attaatctca   1020

attatgccgg agatgctcta agagaaaata cattggtttc agaacatgca caaagagacc   1080

aacgtgaaac acagtgtcaa atgaaggaag ctgaacacat gtatcaaaac gaacaagata   1140

atgtgaacaa acacactgaa cagcaggagt ctctagatca gaaattattt caactacaaa   1200

gcaaaaatat gtggcttcaa cagcaattag ttcatgcaca taagaaagct gacaacaaaa   1260

gcaagataac aattgatatt cattttcttg agaggaaaat gcaacatcat ctcctaaaag   1320

agaaaaatga ggagatattt aattacaata accatttaaa aaaccgtata tatcaatatg   1380

aaaaagagaa agcagaaaca gaaaactcat gagagacaag cagtaagaaa cttcttttgg   1440

agaaacaaca gaccagatct ttactcacaa ctcatgctag gaggccagtc ctagcattac   1500

cttatgttga aaatcttacc aatagtctgt gtcaacagaa tacttatttt agaagaaaaa   1560

ttcatgattt cttcctgaag cctgggcgac agagcgagac tctgtctcaa aaaaaaaaaa   1620

aaaaaaagaa agaaagaaat gcctgtgctt acttcgcttc ccagg                   1665
```

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95

Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160

Val Arg Phe Leu Thr Leu Met Lys Met Lys Ile Ile Ser Tyr Met Lys
                165                 170                 175

Ile Ala Cys
```

<210> SEQ ID NO 180
<211> LENGTH: 1681
<212> TYPE: DNA
<213> ORGANISM: Homo sapien

<400> SEQUENCE: 180

```
gatacagtca ttcttgtgaa agagcaaggg aacttcaaaa agatcactgt gaacaacgta     60

caggaaaaat ggaacaaatg aaaaagaagt tttgtgtact gaaaaagaaa ctgtcagaag    120

caaaagaaat aaaatcacag ttagagaacc aaaaagttaa atgggaacaa gagctctgca    180

gtgtgagatt gactttaaac caagaagaag agaagagaag aaatgccgat atattaaatg    240

aaaaaattag ggaagaatta ggaagaatcg aagagcagca taggaaagag ttagaagtga    300

aacaacaact tgaacaggct ctcagaatac aagatataga attgaagagt gtagaaagta    360

atttgaatca ggtttctcac actcatgaaa atgaaaatta tctcttacat gaaaattgca    420

tgttgaaaaa ggaaattgcc atgctaaaac tggaaatagc cacactgaaa caccaatacc    480

aggaaaagga aaataaatac tttgaggaca ttaagatttt aaaagaaaag aatgctgaac    540

ttcagatgac cctaaaactg aaagaggaat cattaactaa aagggcatct caatatagtg    600

ggcagcttaa agttctgata gctgagaaca caatgctcac ttctaaattg aaggaaaaac    660

aagacaaaga aatactagag gcagaaattg aatcacacca tcctagactg gcttctgctg    720

tacaagacca tgatcaaatt gtgacatcaa gaaaaagtca agaacctgct ttccacattg    780

caggagatgc ttgtttgcaa agaaaaatga atgttgatgt gagtagtacg atatataaca    840
```

-continued

```
atgaggtgct ccatcaacca ctttctgaag ctcaaaggaa atccaaaagc ctaaaaatta    900

atctcaatta tgccggagat gctctaagag aaaatacatt ggtttcagaa catgcacaaa    960

gagaccaacg tgaaacacag tgtcaaatga aggaagctga acacatgtat caaaacgaac   1020

aagataatgt gaacaaacac actgaacagc aggagtctct agatcagaaa ttatttcaac   1080

tacaaagcaa aaatatgtgg cttcaacagc aattagttca tgcacataag aaagctgaca   1140

acaaaagcaa gataacaatt gatattcatt ttcttgagag gaaaatgcaa catcatctcc   1200

taaaagagaa aaatgaggag atatttaatt acaataacca tttaaaaaac cgtatatatc   1260

aatatgaaaa agagaaagca gaaacagaaa actcatgaga gacaagcagt aagaaacttc   1320

ttttggagaa acaacagacc agatctttac tcacaactca tgctaggagg ccagtcctag   1380

cattacctta tgttgaaaaa tcttaccaat agtctgtgtc aacagaatac ttattttaga   1440

agaaaaattc atgatttctt cctgaagcct acagacataa aataacagtg tgaagaatta   1500

cttgttcacg aattgcataa aagctgccca ggatttccat ctaccctgga tgatgccgga   1560

gacatcattc aatccaacca gaatctcgct ctgtcactca ggctggagtg cagtgggcgc   1620

aatctcggct cactgcaact ctgcctccca ggttcacgcc attctctggc acagcctccc   1680

g                                                                   1681


<210> SEQ ID NO 181
<211> LENGTH: 432
<212> TYPE: PRT
<213> ORGANISM: Homo sapien

<400> SEQUENCE: 181

Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220
```

-continued

```
Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350

Ser Leu Asp Gln Lys Leu Phe Gln Leu Gln Ser Lys Asn Met Trp Leu
        355                 360                 365

Gln Gln Gln Leu Val His Ala His Lys Lys Ala Asp Asn Lys Ser Lys
    370                 375                 380

Ile Thr Ile Asp Ile His Phe Leu Glu Arg Lys Met Gln His His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
            420                 425                 430
```